(12) United States Patent
Chang et al.

(10) Patent No.: US 10,070,648 B2
(45) Date of Patent: Sep. 11, 2018

(54) PHOTODYNAMIC INSECTICIDES

(71) Applicant: ROSALIND FRANKLIN UNIVERSITY OF MEDICINE AND SCIENCE, North Chicago, IL (US)

(72) Inventors: Kwang Poo Chang, North Chicago, IL (US); Bala Krishna Kolli, North Chicago, IL (US); Shin-Hong Shiao, Taipei (TW)

(73) Assignees: Rosalind Franklin University of Medicine and Science, North Chicago, IL (US); National Taiwan University, Taipei (TW)

(*) Notice: Subject to any disclaimer, the term of this patent is extended or adjusted under 35 U.S.C. 154(b) by 0 days.

(21) Appl. No.: 15/483,987

(22) Filed: Apr. 10, 2017

(65) Prior Publication Data

US 2017/0295793 A1    Oct. 19, 2017

Related U.S. Application Data

(60) Provisional application No. 62/323,064, filed on Apr. 15, 2016.

(51) Int. Cl.
*A01N 55/02* (2006.01)
*A01N 43/90* (2006.01)
*A01N 55/00* (2006.01)

(52) U.S. Cl.
CPC ............. *A01N 55/02* (2013.01); *A01N 43/90* (2013.01); *A01N 55/00* (2013.01)

(58) Field of Classification Search
CPC ................................. A01N 55/00; A01N 55/02
See application file for complete search history.

(56) References Cited

U.S. PATENT DOCUMENTS

| 2009/0292357 A1 | 11/2009 | McCoy et al. |
| 2010/0113767 A1 | 5/2010 | Gessner et al. |
| 2012/0288524 A1 | 11/2012 | Chang et al. |

OTHER PUBLICATIONS

Yin, Rui, et al., "Light Based Anti-Infectives: Ultraviolet C Irradiation, Photodynamic Therapy, Blue Light, and Beyond", Curr Opin Pharmacol, Oct. 2013, vol. 13(5), pp. 1-43, doi:10.1016/j.coph.2013.08.009.

Abrahamse, Heidi, et al., "New Photosensitizers for Photodynamic Therapy", Biochem. J., 2016, vol. 473, pp. 347-364, doi:10.1042/BJ20150942.

Berenbaum, May, "Phototoxicity of Plant Secondary Metabolites: Insect and Mammalian Perspectives", Archives of Insect Biochemistry and Physiology, 1995, vol. 29, pp. 119-134.

Chang, Kwang Poo, "Vaccination for Disease Prevention and Control: the Necessity of Renewed Emphasis and New Approaches", J. Immunol. Immunotech., 2014, vol. 1(1), pp. 1-4.

Chang, Kwang Poo, "Leishmaniases", In: eLS., John Wiley & Sons, Ltd: Chichester, May 2012, pp. 1-12, doi:10.1002/9780470015902.a0001954.pub3.

Khalil, E.A.G., et al., "Autoclaved Leishmania Major Vaccine for Prevention of Visceral Leishmaniasis: A Randomised, Double-Blind, BCG-Controlled Trial in Sudan", The Lancet, Nov. 4, 2000, vol. 356, pp. 1565-1569.

(Continued)

*Primary Examiner* — San Ming R Hui
(74) *Attorney, Agent, or Firm* — McDonnell Boehnen Hulbert & Berghoff LLP

(57) ABSTRACT

Disclosed herein are photodynamic insecticide methods and compositions for the control or reduction of insect populations comprising the use of photosensitizer compounds in combination with light.

11 Claims, 9 Drawing Sheets

(56) References Cited

OTHER PUBLICATIONS

Li, Hairong, et al., "Syntheses and Properties of a Series of Cationic Water-Soluble Phthalocyanines", J. Med. Chem., 2008, vol. 51, pp. 502-511.
Amor, Thameur Ben, "Sunlight-Activiated Insecticides: Historical Background and Mechanisms of Phototoxic Activity", Insect Biochemistry and Molecular Biology, 2000, vol. 30, pp. 915-925.
Batchu, Ramesh B., et al., "Efficient Lysis of Epithelial Ovarian Cancer Cells by MAGE-A3-Induced Cytotoxic T Lymphocytes Using rAAV-6 Capsid Mutant Vector", Vaccine, 2014, pp. 1-6.
Batchu, R.B., et al., "MAGE-A3 with Cell-Penetrating Domain as an Efficient Therapeutic Cancer Vaccine", JAMA Surg., 2014, vol. 149(5), pp. 451-457, doi:10.1001/jamasurg.2013.4113.
Battersby, Alan R., "Tetrapyrroles: The Pigments of Life", Nat. Prod. Rep., 2000, vol. 17, pp. 507-526, doi:10.1039/b002635m.
Chakravarty, Jaya, et al., "A Clinical Trial to Evaluate the Safety and Immunogenicity of the LEISH-F1 + MPL-SE Vaccine for Use in the Prevention of Visceral Leishmaniasis", Vaccine, 2011, vol. 29, pp. 3531-3537.
Chang, Kwang-Poo, et al., "Leishmania Model for Microbial Virulence: The Relevance of Parasite Multiplication and Pathoantigenicity", Acta Tropica, 2003, vol. 85, pp. 375-390.
Chen, Hui-Wen, et al., "A Multiplex Reverse Transcriptase-PCR Assay for the Genotyping of Avian Infectious Bronchitis Viruses", Avian Diseases, 2010, vol. 54, pp. 104-108.
Elliott, Robert L., "Adjuvant Breast Cancer Vaccine Improves Disease Specific Survival of Breast Cancer Patients with Depressed Lymphocyte Immunity", Surgical Oncology, 2013, vol. 22, pp. 172-177.
Fritsche, Claudia, et al., "Characterization of the Growth Behavior of Leishmania tarentolae—A New Expression System for Recombinant Proteins", Journal of Basic Microbiology, 2007, vol. 47, pp. 384-393.
Gracanin, Michelle, et al., "Singlet-Oxygen-Mediated Amino Acid and Protein Oxidation: Formation of Trytophan Peroxides and Decomposition Products", Free Radical Biology & Medicine, 2009, vol. 47, pp. 92-102.
Gradoni, Luigi, "Canine Leishmania Vaccines: Still a Long Way to Go", Veterinary Parasitology, 2015, vol. 208, pp. 94-100.
Hasspieler, B.M., et al., "Toxicity, Localization and Elimination of the Phototoxin, Alpha-Terthienyl, in Mosquito Larvae", Journal of The American Mosquito Control Association, Dec. 1988, vol. 4(4), pp. 479-484.
Heitz, James Robert, "Pesticidal Applications of Halogenated Xanthene Dyes", Phytoparasitica, 1997, vol. 25(2), pp. 89-92.
Hung, Chen-Hsiung, et al., "m-Benziporphodimethene: A New Porphyrin Analogue Fluorescence Zinc(II) Sensor", Chem. Commun., 2008, pp. 978-980, doi:10.1039/b714412a.
Kamil, A.A., et al., "Alum-Precipitated Autoclaved Leishmania Major Plus Bacille Calmette-Guérrin, a Candidate Vaccine for Visceral Leishmaniasis: Safety, Skin-Delayed Type Hypersensitivity Response and Dose Finding in Healthy Volunteers", Transactions of The Royal Society of Tropical Medicine and Hygiene, 2003, vol. 97, pp. 365-368.
Kotsias, Fiorella, et al, "Reactive Oxygen Species Production in the Phagosome: Impact on Antigen Presentation in Dendritic Cells", Antioxidants & Redox Signaling, 2013, vol. 18(6), pp. 714-729, doi:10.1089/ars.2012.4557.
Llanos-Cuentas, Alejandro, et al., "A Clinical Trial to Evaluate the Safety and Immunogenicity of the LEISH-F1 + MPL-SE Vaccine When Used in Combination with Sodium Stibogluconate for the Treatment of Mucosal Leishmaniasis", Vaccine, 2010, vol. 28, pp. 7427-7435.
Lucht, Jan M., "Public Acceptance of Plant Biotechnology and GM Crops", Viruses, 2015, vol. 7 pp. 4254-4281, doi:10.3390/v7082819.
Mangan, Robert L., et al., "PhotoActive Dye Insecticide Formulations: Adjuvants Increase Toxicity to Mexican Fruit Fly (Diptera: Tephritidae)", J. Econ. Entomol., Feb. 2001, vol. 94(1), pp. 150-156.
Nguyen, Tran Hien, et al., "Field Evaluation of the Establishment Potential of wmelpop Wolbachia in Australia and Vietnam for Dengue Control", Parasites & Vectors, 2015, vol. 8(563), pp. 1-14, doi:10.1186/s13071-015-1174-x.
Nivsarkar, Manish, et al., "Superoxide Dismutase in the Anal Gills of the Mosquito Larvae of *Aedes aegypfi*: Its Inhibition by α-Terthienyl", Archives of Insect Biochemistry and Physiology, 1991, vol. 16, pp. 249-255.
Owusu, Henry F., et al., "Comparability Between Insecticide Resistance Bioassays for Mosquito Vectors: Time to Review Current Methodology?" Parasites & Vectors, 2015, vol. 8(357), pp. 1-11, doi:10.1186/s13071-015-0971-6.
Shelby, Ashley, et al., "Story and Science—How Providers and Parents Can Utilize Storytelling to Combat Anti-Vaccine Misinformation", Human Vaccines & Immunotherapeutics, Aug. 2013, vol. 9(8), pp. 1795-1801.
Shin, N.Y., et al., "Poster Session 4. Molecular Diagnosis & Biomarkers—Targeting to Tumor-Associated Antigen ENO1 Provides Preventive and Therapeutic Effects on Disease Progression of Lung Cancer", Annals of Oncology, 2013, vol. 24 (Supplement 1), pp. i27-i29, doi:10.1093/annonc/mdt046.3.
Tsai, Chi-Wei, et al., "Mealybug Transmission of Grapevine Leafroll Viruses: An Analysis of Virus-Vector Specificity", The American Phytopathological Society, 2010, vol. 100(8), pp. 830-834, doi:10.1094/PHYTO-100-8-0830.
Volf, P., et al., "Establishment and Maintenance of Sand Fly Colonies", Journal of Vector Ecology, Mar. 2011, vol. 36 (Supplemental 1), pp. S1-S9.
Winskill, Peter, et al., "Dispersal of Engineered Male *Aedes aegypti* Mosquitoes", PLoS Neglected Tropical Diseases, 2015, vol. 9(11), e0004156, pp. 1-18, doi:10.1371/journal.pntd.0004156.
Akey, David H., et al., "Continuous Rearing of the Pea Aphid, *Acyrthosiphon pisum*, on a Holidic Diet", Annals of the Entomological Society of America, 1971, vol. 64(2), pp. 353-356.
Duke, Stephen O., et al., "Porphyrin Pesticides—Chemistry, Toxicology, and Pharmaceutical Applications", ACS Symposium Series, 1994.
Heitz, James R., et al., "Light-Activated Pesticides", American Chemical Society Symposium Series, 1987, Table of Contents.
Rebeiz, Constantin A., et al., "Photodynamics of Porphyric Insecticides", Critical Reviews in Plant Sciences, 1995, vol. 14(4), pp. 329-366.
Al-Qahtani, Ahmed, et al., "Aminophthalocyanine-Mediated Photodynamic Inactivation of Leishmania Tropica", Antimicrobial Agents and Chemotherapy, Apr. 2016, vol. 60(4), pp. 2003-2011, doi:10.1128/AAC.01879-15.
Dutta Sujoy, et al., "Combinational Sensitization of Leishmania with Uroporphyrin and Aluminum Phthalocyanine Synergistically Enhances their Photodynamic Inactivation In Vitro and In Vivo", Photochem. Photobiol., May 2012, vol. 88(3), pp. 620-625, doi:10.1111/j.1751-1097.2012.01076.x.
Dutta, Sujoy, et al., "Photodynamic Sensitization of Leishmania Amazonensis in both Extracellular and Intracellular Stages with Aluminum Phthalocyanine Chloride for Photolysis In Vitro", Antimicrobial Agents and Chemotherapy, Nov. 2005, vol. 49(11), pp. 4474-4484, doi:10.1128/AAC.49.11.4474-4484.2005.
Dutta, Sujoy, et al., "Intracellular Targeting Specificity of Novel Phthalocyanines Assessed in a Host-Parasite Model for Developing Potential Photodynamic Medicine", PLoS ONE, Jun. 2011, vol. 6(6), Issue e20786, doi:10.1371/journal.pone.0020786.
Dutta, Sujoy, et al., "Delta-Aminolevulinate-Induced Host-Parasite Porphyric Disparity for Selective Photolysis of Transgenic Leishmania in the Phagolysosomes of Mononuclear Phagocytes: a Potential Novel Platform for Vaccine Delivery", Eukaryotic Cell, Apr. 2012, vol. 11(4), pp. 430-441.
Dutta, Sujoy, et al., "Transgenic Leishmania Model for Delta-Aminolevulinate-Inducible Monospecific Uroporphyria: Cytolytic Phototoxicity Initiated by Singlet Oxygen-Mediated Inactivation of

(56) References Cited

OTHER PUBLICATIONS

Proteins and Its Ablation by Endosomal Mobilization of Cytosolic Uroporphyrin", Eukaryotic Cell, Jul. 2008, vol. 7(7), pp. 1146-1157, doi:10.1128/EC.00365-07.

Dutta, Sujoy, et al., "*Leishmania* spp: Delta-Aminolevulinate-Inducible Neogenesis of Porphyria by Genetic Complementation of Incomplete Heme Biosynthesis Pathway", Exp. Parasitol., Apr. 2008, vol. 118(4), pp. 629-636.

Kumari, Shraddha, et al., "Photodynamic Vaccination of Hamsters with Inducible Suicidal Mutants of Leishmania Amazonensis Elicits Immunity Against Visceral Leishmaniasis", 2009, Eur. J. Immunol., vol. 39, pp. 178-191, doi:10.1002/eji.200838389.

Sah, Jerome F., et al., "Genetic Rescue of Leishmania Deficiency in Porphyrin Biosynthesis Creates Mutants Suitable for Analysis of Cellular Events in Uroporphyria and for Photodynamic Therapy", The Journal of Biological Chemistry, 2002, vol. 277(17), Apr. 2002, pp. 14902-14909.

Benov, Ludmil, "Photodynamic Therapy: Current Status and Future Directions", Med. Princ. Pract., 2015, vol. 24 (Suppl 1), pp. 14-28, doi:10.1159/000362416.

Costa, C.H., et al., "Vaccines for the Leishmaniases: Proposals for a Research Agenda. Working Group on Research Priorities for Development of Leishmaniasis Vaccines", PLos Negl Trop Dis, Mar. 2011, vol. 5(3), e943, doi:10.1371/journal.pntd.0000943.

Chang, KP, et al., "Laboratory Cultivation and Maintenance of Leishmania. In Human Parasitic Diseases", vol. 1 Leishmaniasis, Edited by Chang KP, Bray RS, Amsterdam: Elsevier, 1985, pp. 213-246. (Abstract only).

Kolli, B.K., et al., "Leishmania-Released Nucleoside Diphosphate Kinase Prevents ATP-Mediated Cytolysis of Macrophages", Mol Biochem Parasitol., Apr. 2008, vol. 158(2), pp. 163-75, doi:10.1016/j.molbiopara.2007.12.010, Epub Dec. 25, 2007.

Farrar, J., et al., Manson-Bahr PEC: Manson's Tropical Diseases, 23rd Ed., 1976, Bailiere-Tindall, London. (Abstract only).

Jiang, Xiong-Jie, et al., "Phthalocyanine-Polyamine Conjugates as Highly Efficient Photosensitizers for Photodynamic Therapy", J. Med. Chem., 2011, vol. 54, pp. 320-330, doi:10.1021/jm101253v.

Salama, Elham M., et al., "Site of Action of Hematoporphyrin (a Photo-Activated Insecticide) in Culex pipiens Larvae", Egyptian Journal of Biology, 2002, vol. 4, pp. 133-141.

Thandu, Merlyn, et al., "Phototreatment of Water by Organic Photosensitizers and Comparison with Inorganic Semiconductors", Hindawi Publishing Corporation, International Journal of Photoenergy, Mar. 13, 2015, vol. 2015, Article ID 521367, pp. 1-22, http://dx.doi.org/10.1155/2015/521367.

International Search Report and Written Opinion for PCT/US17/27799, International Searching Authority, dated Apr. 14, 2017, pp. 1-7.

PHOTODYNAMIC INSECTICIDES

CROSS-REFERENCE TO RELATED APPLICATIONS

This application claims the benefit of U.S. Provisional Application No. 62/323,064, filed Apr. 15, 2016, the disclosure of which is hereby incorporated by reference in its entirety.

BACKGROUND

Phytophagous insects cause substantial losses in crops and livestock despite the use of genetically modified (GM) insect-resistant plants. Phloem/xylem sap-feeding insects cause additional damage by transmitting plant diseases. Animal biting insects are of pivotal concern beyond being an annoyance, since many species feed on blood and transmit infectious diseases, accounting for substantial morbidity and mortality of domestic animal and human populations worldwide. Many of these diseases are vector-borne zoonoses, which cannot be eliminated readily.

For example, mosquitoes are significant insect vectors, transmitting many serious infectious diseases, including the recent epidemics of global significance caused by Zika, Dengue, and Chikungunya viruses. The insecticides currently used for mosquito control are toxic and are eventually rendered ineffective due to mosquitos' development of resistance to the insecticides over time.

An alternative approach to control these vectors is to release genetically modified (GM) mosquitoes based on Wolbachia- or male-induced infertility. However, such methods have elicited objections to the use of such genetically modified organisms.

There is thus a need for improved insecticides that are safe and effective.

SUMMARY

This disclosure provides certain advantages and advancements over the prior art, in particular, photodynamic insecticides, which make use of FDA-approved food, drug, fabric and other dyes as photosensitizers for activation with sunlight to generate insecticidal oxygen free radicals. In addition, the disclosure provides dyes of phthalocyanines and porphyrin derivatives with light-activable mosquito larvicidal activities at nanomolar concentrations. The methods and compositions of the disclosure comprise safe and effective means for control of mosquitoes and other harmful insects.

In one aspect, the disclosure provides methods for reducing an insect population, the method comprising: (a) contacting the insect population with a photosensitizer, wherein the photosensitizer is internalized by larval and/or adult insects within the insect population, and wherein the photosensitizer produces reactive oxygen species upon excitation by light; and (b) exposing the photosensitized insect population to light in the presence of oxygen to reduce the insect population.

In some embodiments, the photosensitizer is a phthalocyanine or porphyrin derivative compound. In some embodiments, the photosensitizer is a compound of formula (I):

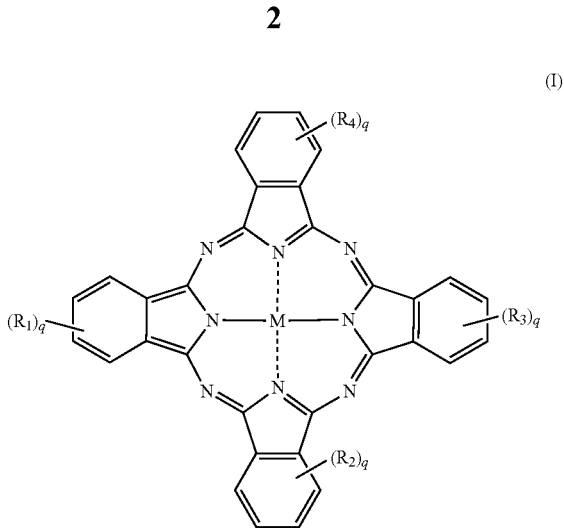

or an acceptable salt thereof, wherein
M is Zn or $Si(L_1)(L_2)$;
$L_1$ and $L_2$ are independently selected from —$O(C_1\text{-}C_6$ alkyl), —$O(C_1\text{-}C_6$ alkenyl), —$O(C_1\text{-}C_6$ alkynyl), —$NH(C_1\text{-}C_6$ alkyl), —$N(C_1\text{-}C_6$ alkyl)$_2$, and —OR, wherein
each R is independently —$[C_1\text{-}C_6$ alkylene-O$]_m$—R', —$[C_1\text{-}C_6$ alkylene-NR"$]_n$—R', or —$Si(R''')_3$,
each m and n are independently an integer selected from 1 to 20,
each R' is independently selected from H and $C_1\text{-}C_6$ alkyl,
each R" is independently selected from H and $C_1\text{-}C_6$ alkyl,
each R''' is independently selected from H, $C_1\text{-}C_6$ alkyl, and aryl;
each q is independently an integer selected from 0, 1, and 2; and
$R_1$, $R_2$, $R_3$, and $R_4$ are independently selected from halogen, $C_1\text{-}C_6$ alkyl, $C_1\text{-}C_6$ alkenyl, $C_1\text{-}C_6$ alkynyl, —$NH(C_1\text{-}C_6$ alkyl), —$N(C_1\text{-}C_6$ alkyl)$_2$, $C_1\text{-}C_6$ alkoxy, $C_1\text{-}C_6$ aryloxy, $C_1\text{-}C_6$ heteroaryloxy, and polyalkylene oxide, each optionally substituted with one or more of halogen, $C_1\text{-}C_6$ alkyl, —OH, $C_1\text{-}C_6$ alkoxy, —$NH_2$, —$NH(C_1\text{-}C_6$ alkyl), —$N(C_1\text{-}C_6$ alkyl)$_2$, —$N(C_1\text{-}C_6$ alkyl)$_3$(I), —$N(C_1\text{-}C_6$ alkyl)$_3$(Cl), or —$N(C_1\text{-}C_6$ alkyl)$_3$ (F).

In some embodiments, the photosensitizer is a compound of formula (II):

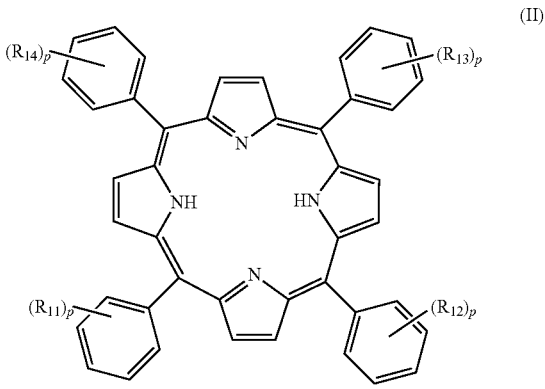

or an acceptable salt thereof, wherein each p is independently an integer selected from 0, 1, and 2; and $R_{11}$, $R_{12}$, $R_{13}$, and $R_{14}$ are independently selected from the group consisting of: halogen, $C_1$-$C_6$ alkyl, $C_1$-$C_6$ alkenyl, $C_1$-$C_6$ alkynyl, $C_1$-$C_6$ alkoxy, —NH($C_1$-$C_6$ alkyl), —N($C_1$-$C_6$ alkyl)$_2$, —N($C_1$-$C_6$ alkyl)$_3$(I), —N($C_1$-$C_6$ alkyl)$_3$(Cl), —N($C_1$-$C_6$ alkyl)$_3$(F), —S(O)$_2$(OH), and —S(O)$_2$($C_1$-$C_6$ alkoxy).

In some embodiments, the photosensitizer is selected from the group consisting of: rose bengal, cyanosine, PC1, PC2, PC3.4, PC14, TMAP, and TPPS2. In some embodiments, the photosensitizer is selected from the group consisting of PC1, PC2, PC3.4, and PC14. In some embodiments, the light is white light or red light. In some embodiments, the wavelength of the light is less than about 600 nm. In some embodiments, the insect population comprises *Anopheles* spp., *Aedes* spp., *Culex* spp., *Cocquilletidia* spp., *Phlebotomus* spp., *Simulium* spp., or *Culicoides* spp. insects. In some embodiments, the insect population comprises hematophagus insects. In some embodiments, the photosensitizer is internalized by $2^{nd}$, $3^{rd}$, and/or $4^{th}$ instar larval insects.

In another aspect, the disclosure provides insecticidal compositions comprising a photosensitizer selected from the group consisting of: rose bengal, cyanosine, TMAP, TPPS2, a porphyrin derivative compound, a compound of formula (I), and a compound of formula (II), wherein the compound of formula (I) is:

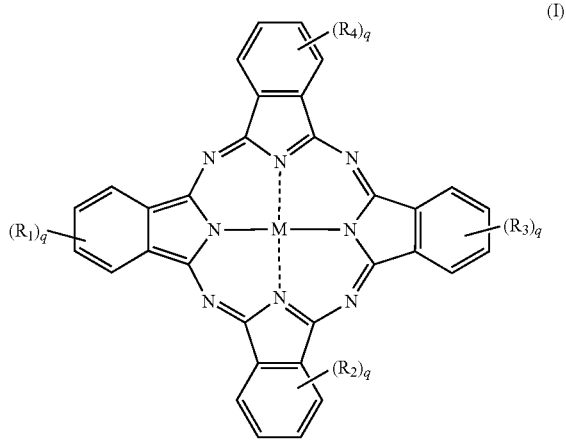

(I)

or an acceptable salt thereof, wherein

M is Zn or Si($L_1$)($L_2$);

$L_1$ and $L_2$ are independently selected from —O($C_1$-$C_6$ alkyl), —O($C_1$-$C_6$ alkenyl), —O($C_1$-$C_6$ alkynyl), —NH($C_1$-$C_6$ alkyl), —N($C_1$-$C_6$ alkyl)$_2$, and —OR, wherein each R is independently —[$C_1$-$C_6$ alkylene-O]$_m$—R', —[$C_1$-$C_6$ alkylene-NR"]$_n$—R', or —Si(R''')$_3$, each m and n are independently an integer selected from 1 to 20, each R' is independently selected from H and $C_1$-$C_6$ alkyl, each R" is independently selected from H and $C_1$-$C_6$ alkyl, each R''' is independently selected from H, $C_1$-$C_6$ alkyl, and aryl;

each q is independently an integer selected from 0, 1, and 2; and $R_1$, $R_2$, $R_3$, and $R_4$ are independently selected from halogen, $C_1$-$C_6$ alkyl, $C_1$-$C_6$ alkenyl, $C_1$-$C_6$ alkynyl, —NH($C_1$-$C_6$ alkyl), —N($C_1$-$C_6$ alkyl)$_2$, $C_1$-$C_6$ alkoxy, $C_1$-$C_6$ aryloxy, $C_1$-$C_6$ heteroaryloxy, and polyalkylene oxide, each optionally substituted with one or more of halogen, $C_1$-$C_6$ alkyl, —OH, $C_1$-$C_6$ alkoxy, —NH$_2$, —NH($C_1$-$C_6$ alkyl), —N($C_1$-$C_6$ alkyl)$_2$, —N($C_1$-$C_6$ alkyl)$_3$(I), —N($C_1$-$C_6$ alkyl)$_3$(Cl), or —N($C_1$-$C_6$ alkyl)$_3$ (F); and wherein the compound of formula (II) is:

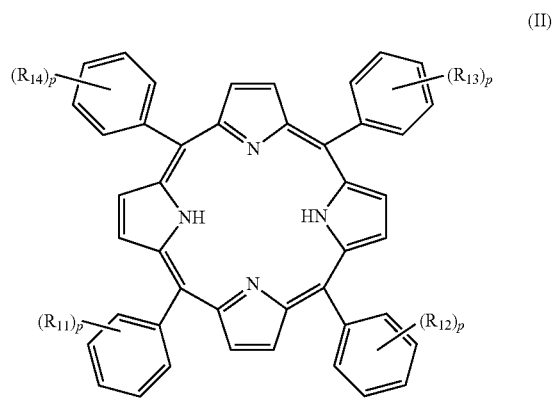

(II)

or an acceptable salt thereof, wherein each p is independently an integer selected from 0, 1, and 2; and $R_{11}$, $R_{12}$, $R_{13}$, and $R_{14}$ are independently selected from the group consisting of: halogen, $C_1$-$C_6$ alkyl, $C_1$-$C_6$ alkenyl, $C_1$-$C_6$ alkynyl, $C_1$-$C_6$ alkoxy, —NH($C_1$-$C_6$ alkyl), —N($C_1$-$C_6$ alkyl)$_2$, —N($C_1$-$C_6$ alkyl)$_3$(I), —N($C_1$-$C_6$ alkyl)$_3$(Cl), —N($C_1$-$C_6$ alkyl)$_3$(F), —S(O)$_2$(OH), and —S(O)$_2$($C_1$-$C_6$ alkoxy).

In some embodiments, the photosensitizer is rose bengal, cyanosine, PC1, PC2, PC3.4, PC14, TMAP, or TPPS2.

In some embodiments of any of the methods and compositions of the disclosure, the compounds of formula (I) are of formula:

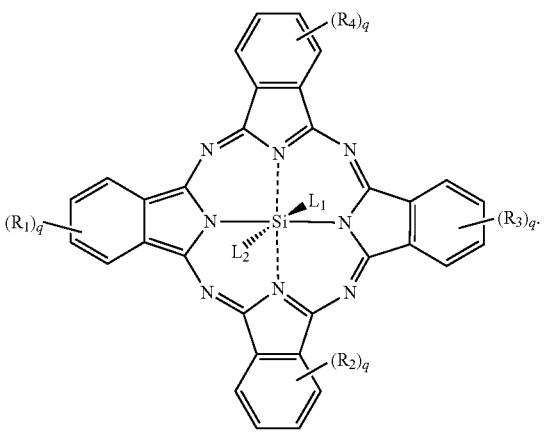

In some embodiments of any of the methods and compositions of the disclosure, the compounds of formula (I) are of formula:

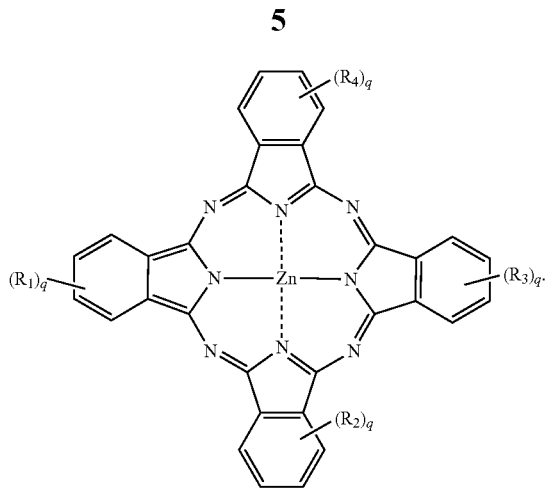

In some embodiments of any of the methods and compositions of the disclosure, each q in formula (I) is an integer selected from 0 and 1. In some embodiments, $L_1$ and $L_2$ are independently selected from —O($C_1$-$C_6$ alkyl), —O($C_1$-$C_6$ alkenyl), —O($C_1$-$C_6$ alkynyl), and —OR. In some embodiments, each R is independently —[$C_1$-$C_6$ alkylene-NR"]$_n$—R', or -[ethylene-NR"]$_n$—R', or -[propylene-NR"]$_n$—R'; wherein R" is hydrogen or methyl, or R" is hydrogen; and wherein R' is hydrogen or methyl, or R' is hydrogen, or R' is methyl. In some embodiments, n is an integer selected from 1 to 6, or from 1 to 5, or from 1 to 4, or from 1 to 3, or n is 1, 2, or 3, or n is 1, or n is 2, or n is 3. In some embodiments, each R is independently —Si(R''')$_3$, wherein R''' is independently selected from H, $C_1$-$C_6$ alkyl, and aryl; or wherein R''' is independently selected from $C_1$-$C_6$ alkyl and aryl. In some embodiments, $L_1$ and $L_2$ are independently selected from:

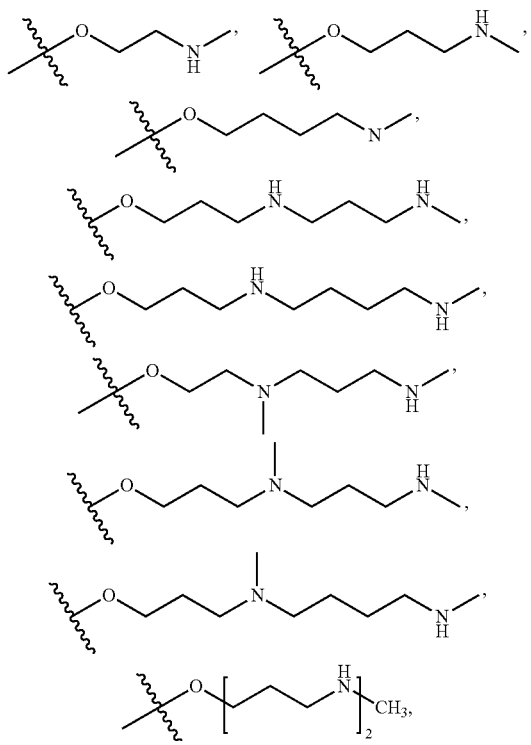

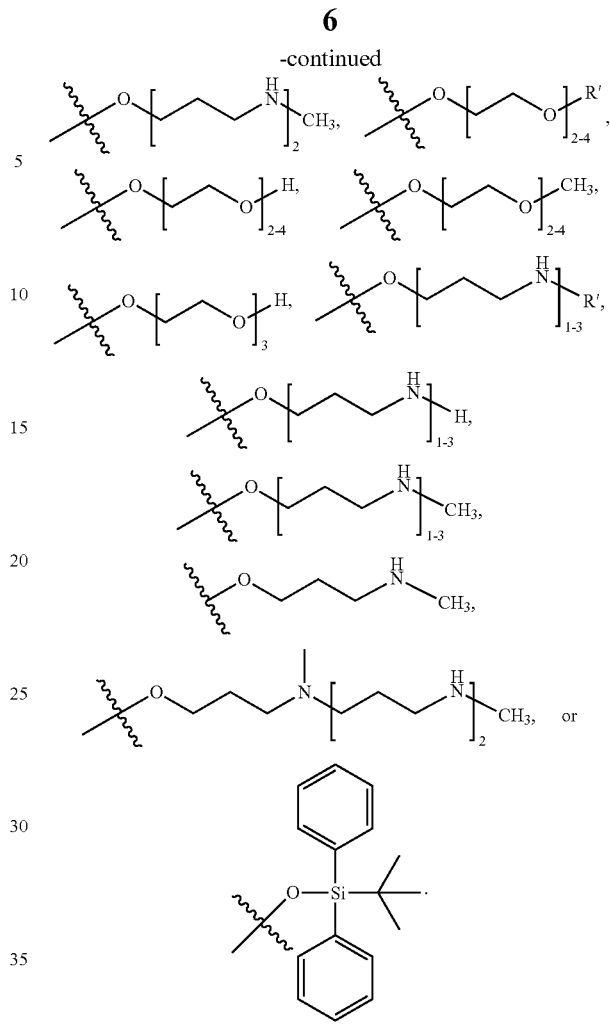

In some embodiments, $L_1$ and $L_2$ are the same.

In some embodiments of any of the methods and compositions of the disclosure, the compounds of formula (II) are a salt of the formula:

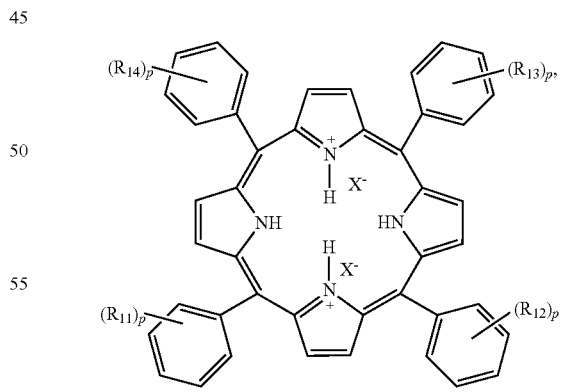

wherein X$^-$ is a suitable counter ion, such as Cl$^-$ or I$^-$.

In some embodiments of any of the methods and compositions of the disclosure, each p in formula (II) is an integer selected from 0 and 1. In one embodiment, each p is 1. In one embodiment, each p is 0. In one embodiment, the compounds of formula (II) are of the formula:

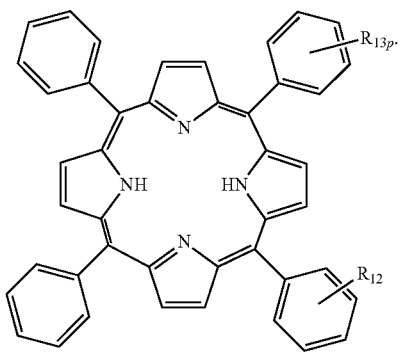

or an acceptable salt thereof.

In some embodiments of any of the methods and compositions of the disclosure, the compounds of formula (II) are wherein $R_{11}$, $R_{12}$, $R_{13}$, and $R_{14}$ are independently selected from the group consisting of: $C_1$-$C_6$ alkyl, $C_1$-$C_6$ alkoxy, —N($C_1$-$C_6$ alkyl)$_2$, —N($C_1$-$C_6$ alkyl)$_3$(I), —N($C_1$-$C_6$ alkyl)$_3$(Cl), —N($C_1$-$C_6$ alkyl)$_3$(F), —S(O)$_2$(OH), and —S(O)$_2$($C_1$-$C_6$ alkoxy). In one embodiment, $R_{11}$, $R_{12}$, $R_{13}$, and $R_{14}$ are independently selected from the group consisting of: $C_1$-$C_6$ alkyl, —N($C_1$-$C_6$ alkyl)$_3$(I), —N($C_1$-$C_6$ alkyl)$_3$(Cl), —N($C_1$-$C_6$ alkyl)$_3$(F), —S(O)$_2$(OH), and —S(O)$_2$($C_1$-$C_6$ alkoxy). In one embodiment, $R_{11}$, $R_{12}$, $R_{13}$, and $R_{14}$ are independently selected from the group consisting of —N($C_1$-$C_6$ alkyl)$_3$(I), —N($C_1$-$C_6$ alkyl)$_3$(Cl), —N($C_1$-$C_6$ alkyl)$_3$(F), and —S(O)$_2$(OH). In one embodiment, each $R_{11}$, $R_{12}$, $R_{13}$, and $R_{14}$ (if present) is —N($C_1$-$C_6$ alkyl)$_3$(I) or —N($C_1$-$C_6$ alkyl)$_3$(Cl). In one embodiment, each $R_{11}$, $R_{12}$, $R_{13}$, and $R_{14}$ (if present) is —S(O)$_2$(OH).

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, in which:

FIG. 4A shows instar-specific sensitivity of *Aedes* mosquito larvae to light-activated TPPS2; FIG. 4B shows instar-specific sensitivity of *Aedes* mosquito larvae to light-activated TMAP; FIG. 4C shows instar-specific sensitivity of *Aedes* mosquito larvae to light-activated PC1; FIG. 4D shows instar-specific sensitivity of *Aedes* mosquito larvae to light-activated PC14; and FIG. 4E shows instar-specific sensitivity of *Aedes* mosquito larvae to light-activated Rose Bengal.

DETAILED DESCRIPTION

Figure 1:
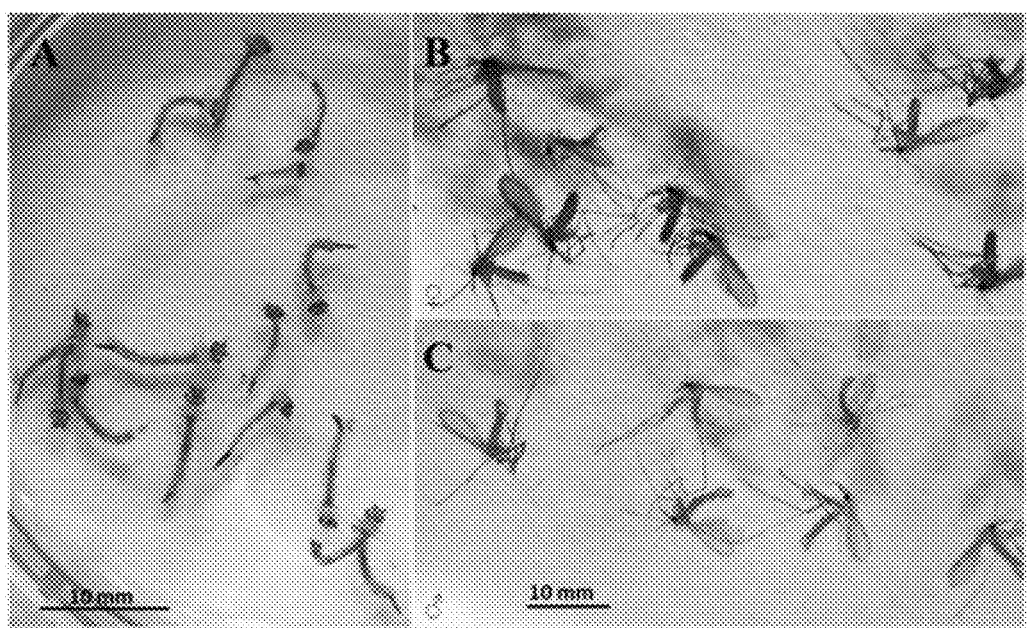
FIG. 1 shows uptake of rose bengal by vector insects and their photo-inactivation. Panel [A]: *Culex pipiens quinquefasciatus* 4th instar larvae exposed to rose Bengal (10 µg/mL) (~20 larvae/5 mL water/well in 6-well plate) in dark for ~24 hours followed by exposure to white light for ~6 hrs at ~2500 lux. Panels [B] and [C]: *Phlebotomus duboscqi* female (B) and male (C) adult flies (~20 flies/screened paper cup) fed with 5% sucrose solution and 500 µL of 5 mg/mL rose bengal in a cotton ball for ~20 hrs in the dark followed by exposure to ~2500 lux of white light for 3 hrs. Duplicate samples were prepared and kept in the dark as controls. Rose bengal was taken up by the mosquito larvae and sand flies of both sexes.

All publications, patents and patent applications cited herein are hereby expressly incorporated by reference for all purposes.

Before describing the present invention in detail, a number of terms will be defined. As used herein, the singular forms "a", "an", and "the" include plural referents unless the context clearly dictates otherwise. For example, reference to a "protein" means one or more proteins.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the term "photodynamic therapy" (PDT) refers to the use of dyes as photosensitizers (PSs), which can be activated by light to produce oxidative biocidal radicals in the presence of atmospheric oxygen.

The disclosure provides PS-mediated photodynamic insecticides (PDI) for control of insect vectors, such as, but not limited to mosquitoes of *Anopheles* spp., which transmit malaria, and *Aedes* spp., which transmit Chikungunya, Dengue, and Zika fever, responsible for contemporary epidemics of these dangerous diseases in the tropical/subtropical world.

In principle, PS-sensitization of all insects is possible by direct spraying for their uptake via surface contact and/or systematically via the hosts, as used for the current insecticides. Direct incorporation of PS into the drinking and food sources of insects will deliver them into the digestive tracts for sensitization of cells therein. In both cases, accessibility of PS-sensitized cells to light is necessary to generate cytotoxic oxygen free radicals for target destruction. Nocturnal and darkness-loving insects are less amenable to PDT unless a light-emitter is provided with the PS for their excitation.

For example, to apply PDT against female mosquitoes and other blood feeders (phototropic and day-light active species), PS is amenable to delivery via the bloodstream of susceptible hosts or the use of suitable baits to sensitize the insects for inactivation by sunlight. The larval stages of all mosquitoes (and also black flies) are aquatic and thus are receptive to water-soluble PS for PDT.

Light is known to excite photosensitizers (PS) to produce cytotoxic reactive oxygen species (ROS) in presence of atmospheric oxygen. This modality is attractive for designing control measures against vector insects transmitting plant and animal diseases. Many PSs have a proven record of safety, since they have been already in clinical use or used as food, cosmetic and fabric dyes. In addition, the cytotoxicity of ROS so produced selects no resistant mutants in contrast to other drugs and pesticides.

In one aspect, the disclosure provides methods for reducing an insect population, the method comprising: (a) contacting the insect population with a photosensitizer, wherein the photosensitizer is internalized intracellularly by larval and/or adult insects within the insect population, and wherein the photosensitizer produces reactive oxygen species upon excitation by light; and (b) exposing the photosensitized insect population to light in the presence of oxygen, such as atmospheric oxygen, to reduce the insect population.

As used herein, the term "photosensitizers" (PSs) refers to ring compounds or dyes, which are light-excitable, and which produce cytotoxic reactive oxygen species (ROS), particularly singlet oxygen which is formed in the presence of oxygen. Examples of naturally occurring PSs are macrocyclic tetrapyrroles essential to all aerobic cells, e.g. corrins, chlorins, and porphyrins, which are intermediate products during the biosynthesis of vitamin B12, chlorophyll, and heme as "pigments of life." During the evolution of their biosynthetic pathways, the stoichiometry of these intermediates is stringently regulated by necessity to minimize their phototoxicity. Many plants also produce PSs as secondary metabolites for self-protection, e.g. psoralen and hypericin. Other PSs are chemically synthesized, e.g. analogues of fluorescein, rose bengal, and cyanosine, as well as macrocycles, including phthalocyanines (PCs). Natural and synthetic PSs include FDA-approved drugs in clinical uses and dyes for coloring cosmetic products, food stuff, fabrics, drugs and many other everyday consumables.

As used herein, the term "controlling" when used in reference to an insect population or plurality of insects refers to preventing the growth of, and preferably reducing, the number of individuals comprising the insect population. Control and/or reduction of an insect population can be achieved by killing or incapacitating adult individuals, as well as by killing or incapacitating larval individuals.

In some embodiments of the aspects disclosed herein, the photosensitizer is a phthalocyanine or porphyrin derivative compound. In some embodiments, the photosensitizer is a compound of formula (I):

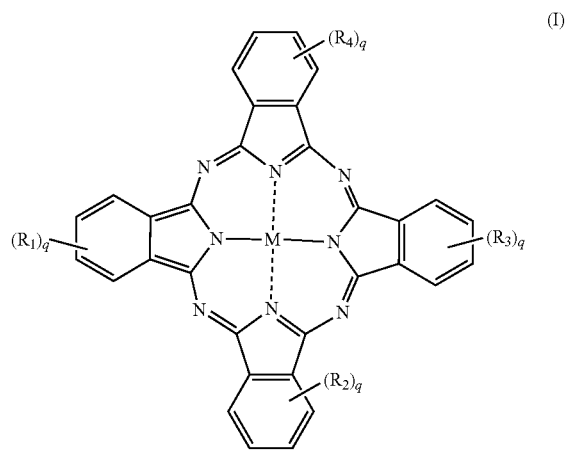

or an acceptable salt thereof, wherein
M is Zn or $Si(L_1)(L_2)$;
$L_1$ and $L_2$ are independently selected from —O($C_1$-$C_6$ alkyl), —O($C_1$-$C_6$ alkenyl), —O($C_1$-$C_6$ alkynyl), —NH($C_1$-$C_6$ alkyl), —N($C_1$-$C_6$ alkyl)$_2$, and —OR, wherein
each R is independently —[$C_1$-$C_6$ alkylene-O]$_m$—R', —[$C_1$-$C_6$ alkylene-NR'']$_n$—R', or —Si(R''')$_3$,
each m and n are independently an integer selected from 1 to 20,
each R' is independently selected from H and $C_1$-$C_6$ alkyl,
each R'' is independently selected from H and $C_1$-$C_6$ alkyl,
each R''' is independently selected from H, $C_1$-$C_6$ alkyl, and aryl;
each q is independently an integer selected from 0, 1, and 2; and
$R_1$, $R_2$, $R_3$, and $R_4$ are independently selected from halogen, $C_1$-$C_6$ alkyl, $C_1$-$C_6$ alkenyl, $C_1$-$C_6$ alkynyl, —NH($C_1$-$C_6$ alkyl), —N($C_1$-$C_6$ alkyl)$_2$, $C_1$-$C_6$ alkoxy, $C_1$-$C_6$ aryloxy, $C_1$-$C_6$ heteroaryloxy, and polyalkylene oxide, each optionally substituted with one or more of halogen, $C_1$-$C_6$ alkyl, —OH, $C_1$-$C_6$ alkoxy, —NH$_2$, —NH($C_1$-$C_6$ alkyl), —N($C_1$-$C_6$ alkyl)$_2$, —N($C_1$-$C_6$ alkyl)$_3$(I), —N($C_1$-$C_6$ alkyl)$_3$(Cl), or —N($C_1$-$C_6$ alkyl)$_3$ (F).

In some embodiments, the photosensitizer is a compound of formula (II):

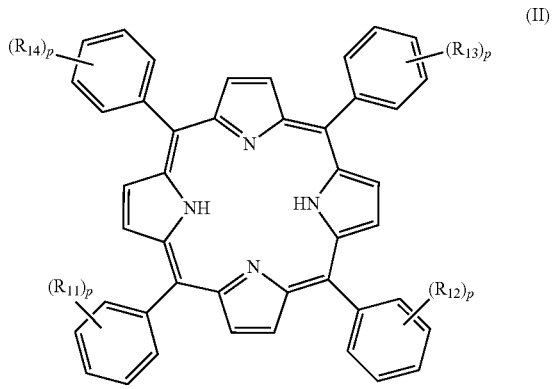

or an acceptable salt thereof, wherein each p is independently an integer selected from 0, 1, and 2; and $R_{11}$, $R_{12}$, $R_{13}$, and $R_{14}$ are independently selected from the group consisting of: halogen, $C_1$-$C_6$ alkyl, $C_1$-$C_6$ alkenyl, $C_1$-$C_6$ alkynyl, $C_1$-$C_6$ alkoxy, —NH($C_1$-$C_6$ alkyl), —N($C_1$-$C_6$ alkyl)$_2$, —N($C_1$-$C_6$ alkyl)$_3$(I), —N($C_1$-$C_6$ alkyl)$_3$(Cl), —N($C_1$-$C_6$ alkyl)$_3$(F), —S(O)$_2$(OH), and —S(O)$_2$($C_1$-$C_6$ alkoxy).

In some embodiments, the photosensitizer is selected from the group consisting of: rose bengal, cyanosine, PC1, PC2, PC3.4, PC14, TMAP, and TPPS2.

In some embodiments, the photosensitized insect population is exposed to white light or red. As used herein, the terms "irradiate" and "expose to light" are interchangeable and refer to any means of exposing a cell, subject, or system to light, such as visible light, UV light, and infrared light. Typically, in the aspects and embodiments disclosed herein, the light is visible light. In some embodiments, the light is white light or sun light, inclusive of all effective wavelengths for the PSs disclosed herein, and/or the particular PS(s) being used. In some embodiments, the light is red light. In some embodiments, the wavelength of the light is less than about 600 nm. In some embodiments, the wavelength or wavelengths of the light comprise the particular excitation wavelengths of the particular PS or PSs being used in a particular instance. In some embodiments, the light is dim light.

In some embodiments, the insect population comprises *Anopheles* spp., *Aedes* spp., *Culex* spp., *Cocquilletidia* spp., *Phlebotomus* spp., *Simulium* spp., or *Culicoides* spp. insects. In some embodiments, the insect population comprises hematophagus insects.

In some embodiments, the photosensitizer is internalized by adult insects within the insect population. In some embodiments, the photosensitizer is internalized by insect larvae within the insect population. In some embodiments, the photosensitizer is internalized by $2^{nd}$, $3^{rd}$, and/or $4^{th}$ instar larval insects.

In another aspect, the disclosure provides insecticidal compositions comprising a photosensitizer selected from the group consisting of: rose bengal, cyanosine, a compound of formula (I), and a compound of formula (II), wherein the compound of formula (I) is:

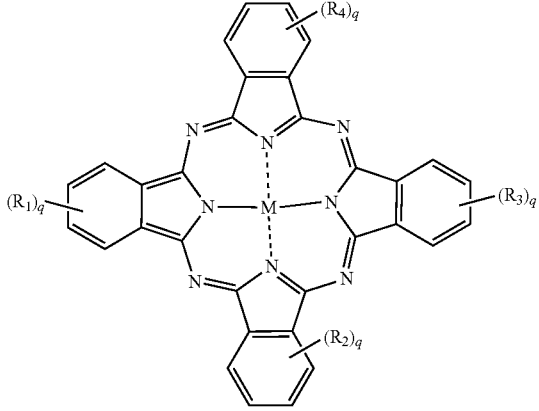

(I)

or an acceptable salt thereof, wherein

M is Zn or Si($L_1$)($L_2$);

$L_1$ and $L_2$ are independently selected from —O($C_1$-$C_6$ alkyl), —O($C_1$-$C_6$ alkenyl), —O($C_1$-$C_6$ alkynyl), —NH($C_1$-$C_6$ alkyl), —N($C_1$-$C_6$ alkyl)$_2$, and —OR, wherein each R is independently —[$C_1$-$C_6$ alkylene-O]$_m$—R', —[$C_1$-$C_6$ alkylene-NR"]$_n$—R', or —Si(R''')$_3$, each m and n are independently an integer selected from 1 to 20, each R' is independently selected from H and $C_1$-$C_6$ alkyl, each R" is independently selected from H and $C_1$-$C_6$ alkyl, each R''' is independently selected from H, $C_1$-$C_6$ alkyl, and aryl;

each q is independently an integer selected from 0, 1, and 2; and $R_1$, $R_2$, $R_3$, and $R_4$ are independently selected from halogen, $C_1$-$C_6$ alkyl, $C_1$-$C_6$ alkenyl, $C_1$-$C_6$ alkynyl, —NH($C_1$-$C_6$ alkyl), —N($C_1$-$C_6$ alkyl)$_2$, $C_1$-$C_6$ alkoxy, $C_1$-$C_6$ aryloxy, $C_1$-$C_6$ heteroaryloxy, and polyalkylene oxide, each optionally substituted with one or more of halogen, $C_1$-$C_6$ alkyl, —OH, $C_1$-$C_6$ alkoxy, —NH$_2$, —NH($C_1$-$C_6$ alkyl), —N($C_1$-$C_6$ alkyl)$_2$, —N($C_1$-$C_6$ alkyl)$_3$(I), —N($C_1$-$C_6$ alkyl)$_3$(Cl), or —N($C_1$-$C_6$ alkyl)$_3$ (F); and wherein the compound of formula (II) is:

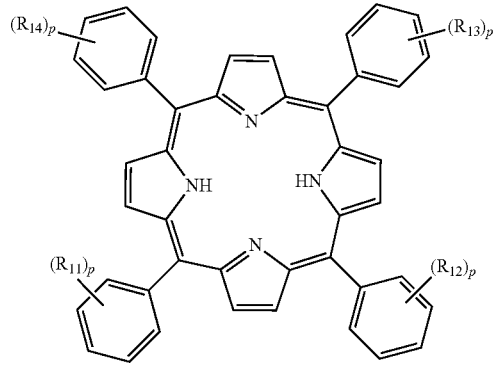

(II)

or an acceptable salt thereof, wherein each p is independently an integer selected from 0, 1, and 2; and $R_{11}$, $R_{12}$, $R_{13}$, and $R_{14}$ are independently selected from the group consisting of: halogen, $C_1$-$C_6$ alkyl, $C_1$-$C_6$ alkenyl, $C_1$-$C_6$ alkynyl, $C_1$-$C_6$ alkoxy, —NH($C_1$-$C_6$ alkyl), —N($C_1$-$C_6$ alkyl)$_2$, —N($C_1$-$C_6$ alkyl)$_3$(I), —N($C_1$-$C_6$ alkyl)$_3$(Cl), —N($C_1$-$C_6$ alkyl)$_3$(F), —S(O)$_2$(OH), and —S(O)$_2$($C_1$-$C_6$ alkoxy).

In some embodiments of the compositions disclosed herein, the photosynthesizer is rose bengal, cyanosine, PC1, PC2, PC3.4, PC14, TMAP, or TPPS2.

In some embodiments of any of the above aspects relating to the methods and compositions disclosed herein, the compounds of formula (I) are of formula:

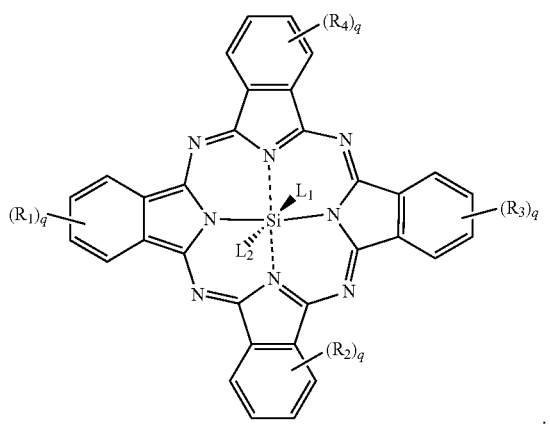

In some embodiments, the compounds of formula (I) are of the formula:

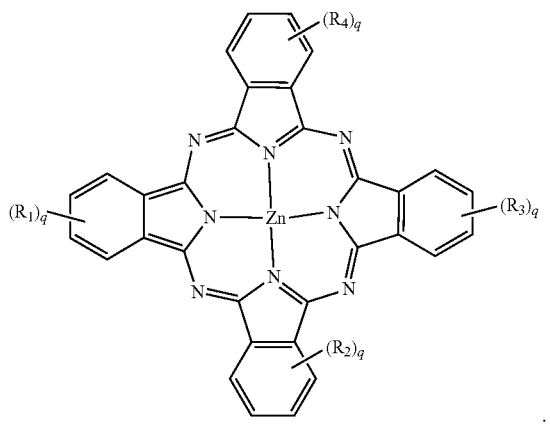

In some embodiments, each q in formula (I) is an integer selected from 0 and 1. In some embodiments, $L_1$ and $L_2$ are independently selected from —O($C_1$-$C_6$ alkyl), —O($C_1$-$C_6$ alkenyl), —O($C_1$-$C_6$ alkynyl), and —OR. In some embodiments, each R is independently —[$C_1$-$C_6$ alkylene-NR"]$_n$—R', or -[ethylene-NR"]$_n$—R', or -[propylene-NR"]$_n$—R'; wherein R" is hydrogen or methyl, or R" is hydrogen; and wherein R' is hydrogen or methyl, or R' is hydrogen, or R' is methyl. In some embodiments, n is an integer selected from 1 to 6, or from 1 to 5, or from 1 to 4, or from 1 to 3, or n is 1, 2, or 3, or n is 1, or n is 2, or n is 3. In some embodiments, each R is independently —Si(R''')$_3$, wherein R''' is independently selected from H, $C_1$-$C_6$ alkyl, and aryl; or wherein R''' is independently selected from $C_1$-$C_6$ alkyl and aryl. In some embodiments, $L_1$ and $L_2$ are independently selected from:

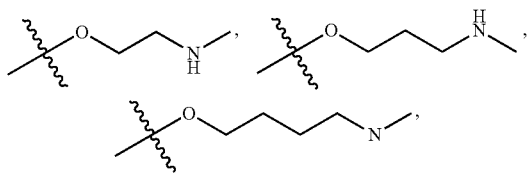

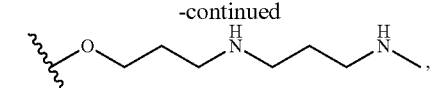

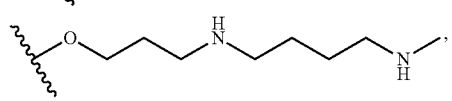

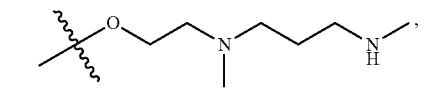

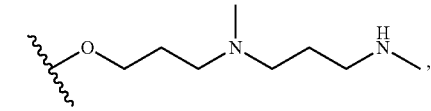

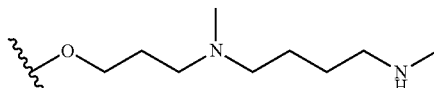

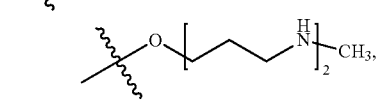

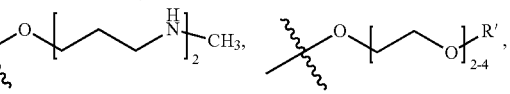

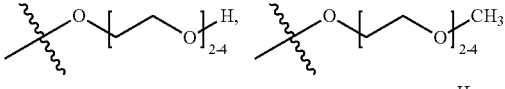

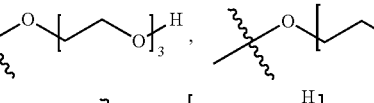

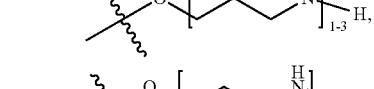

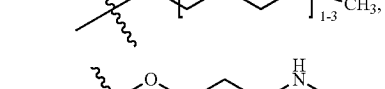

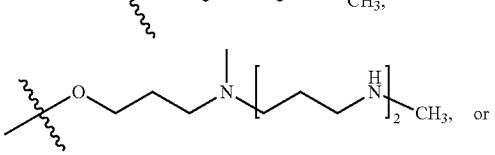

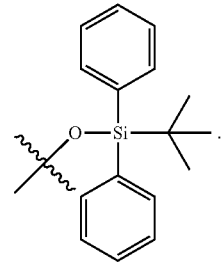 [SMILES: *O[Si](c1ccccc1)(c1ccccc1)C(C)(C)C]

In some embodiments, $L_1$ and $L_2$ are the same.

In some embodiments of any of the methods and compositions of the disclosure, the compound of formula (I) is PC1, PC2, PC14, or PC3.4.

In some embodiments of any of the methods and compositions of the disclosure, the compounds of formula (II) are a salt of the formula:

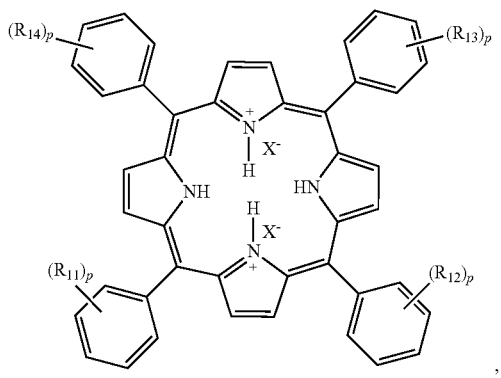

wherein $X^-$ is a suitable counter ion, such as $Cl^-$ or $I^-$. In some embodiments of any of the methods and compositions of the disclosure, each p in formula (II) is an integer selected from 0 and 1. In one embodiment, each p is 1. In one embodiment, each p is 0. In one embodiment, the compounds of formula (II) are of the formula:

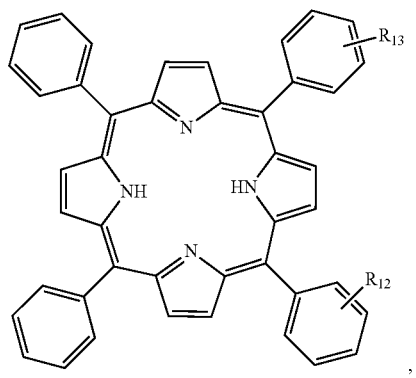

or an acceptable salt thereof. In some embodiments of any of the methods and compositions of the disclosure, the compounds of formula (II) are wherein $R_{11}$, $R_{12}$, $R_{13}$, and $R_{14}$ are independently selected from the group consisting of: $C_1$-$C_6$ alkyl, $C_1$-$C_6$ alkoxy, —$N(C_1$-$C_6$ alkyl)$_2$, —$N(C_1$-$C_6$ alkyl)$_3$(I), —$N(C_1$-$C_6$ alkyl)$_3$(Cl), —$N(C_1$-$C_6$ alkyl)$_3$(F), —$S(O)_2$(OH), and —$S(O)_2(C_1$-$C_6$ alkoxy). In one embodiment, $R_{11}$, $R_{12}$, $R_{13}$, and $R_{14}$ are independently selected from the group consisting of: $C_1$-$C_6$ alkyl, —$N(C_1$-$C_6$ alkyl)$_3$(I), —$N(C_1$-$C_6$ alkyl)$_3$(Cl), —$N(C_1$-$C_6$ alkyl)$_3$(F), —$S(O)_2$(OH), and —$S(O)_2(C_1$-$C_6$ alkoxy). In one embodiment, $R_{11}$, $R_{12}$, $R_{13}$, and $R_{14}$ are independently selected from the group consisting of —$N(C_1$-$C_6$ alkyl)$_3$(I), —$N(C_1$-$C_6$ alkyl)$_3$(Cl), —$N(C_1$-$C_6$ alkyl)$_3$(F), and —$S(O)_2$(OH). In one embodiment, each $R_{11}$, $R_{12}$, $R_{13}$, and $R_{14}$ (if present) is —$N(C_1$-$C_6$ alkyl)$_3$(I) or —$N(C_1$-$C_6$ alkyl)$_3$(Cl). In one embodiment, each $R_{11}$, $R_{12}$, $R_{13}$, and $R_{14}$ (if present) is —$S(O)_2$(OH).

In some embodiments of any of the methods and compositions of the disclosure, the compound of formula (II) is TMAP or TPPS2.

In some embodiments of any of the methods and compositions of the disclosure, the photosensitizers are present in a composition or applied to target insects at a concentration of from about 0.5 μM to about 60 μM. In some embodiments, the photosensitizer is present at a concentration of from about 0.1 μM to about 10 μM, or from about 1 μM to about 10 μM, or from about 1 μM to about 1 μM. In some embodiments, the photosensitizer is rose bengal or cyanosine, present at a concentration of from about 1 μM to about 50 μM, or from about 6 μM to about 60 μM. In some embodiments, the photosensitizer is a phthalocyanine, such as PC1, PC2, PC14, or PC3.4, present at a concentration of from about 0.1 μM to about 10 μM, or from about 1 μM to about 10 μM. In some embodiments, the photosensitizer is a porphyrin derivative compound, such as TMAP or TPPS2, present at a concentration of from about 0.1 μM to about 10 μM, or from about 0.2 μM to about 2 μM, or from about 1 μM to about 2 μM.

The application of PDT to eliminate pests is based on ROS production after illumination of PSs at their specific excitation wavelengths. Initially generated are largely singlet oxygen ($^1O_2$) or hydroxyl radicals or both, leading to the secondary production of additional ROS, including peroxides and superoxides. While all ROS are short-lived, $^1O_2$ is especially transient. It does not travel the distance spanning the lipid bilayer of, for example, a cell membrane due to its extremely short half-life of 2-3 microseconds. Thus, while $^1O_2$ is highly active and most destructive, it reacts only with biomolecules in the immediate vicinity of the site of its generation. In addition, $^1O_2$ is a known by-product of photosynthesis in plants, but not produced by non-photosynthetic mammals, insects, and other organisms such as protozoa, for example, *Leishmania*. Inefficiency of cells of such mammals, insects, and other organisms to detoxify $^1O_2$ is thus expected, rendering them particularly susceptible to its oxidative damage. In contrast to $^1O_2$, peroxides/superoxides are disposed of efficiently by multiple mechanisms in all aerobic cells. Singlet oxygen generated by light excitation of porphyrins and phthalocyanines thus has the potential for strategic deployment to inflict maximal destruction of specific harmful targets with minimal collateral damage to beneficial ones.

PDT, especially using $^1O_2$ generating PSs for non-photosynthetic cells, is unlikely to select for resistance, since neither light nor PS alone is cytotoxic and thus non-selective. Their use in combination produces a burst of ROS against multiple targets, minimizing the likelihood of selecting all for resistance.

The effectiveness of PDT is theoretically a function of light intensity delivered at the wavelength specific to a particular PS and the quantum yield of the PS. Under physiological conditions, however, PDT is dependent on the uptake of PSs by the target cells.

Bioavailability of PSs in relation to their cellular uptake varies with their chemical structures. Some PSs, like phthalocyanine compounds (PCs), are amenable to chemical engineering for modifications of their coordinating metals, side-chains, and/or axial ligands, rendering them more cationic for affinity to the negatively charged cell surface and more soluble for persistence in the milieu.

Insects and insect populations may be exposed to the PS-containing compositions of the disclosure though any means by which the PS or PSs within the composition remain inactive while internalized by the insects, and further remain inactive until the photosensitized insect populations are exposed to light. Non-limiting examples of routes of exposure include the inclusion of PS in water or food sources (such as bait or drinking water), leading to internalization of PS by insects through consumption; mixing of PS compositions into the media or liquid in which insects are living, leading to uptake through, for example, absorption, adsorption, diffusion, etc.; spraying of insect populations with PS compositions in solution, leading to uptake though, for example, absorption, adsorption, diffusion, etc., such as when the compositions of the disclosure are delivered by, for example, aerosol mist dispenser or sprayer.

Figure 2:
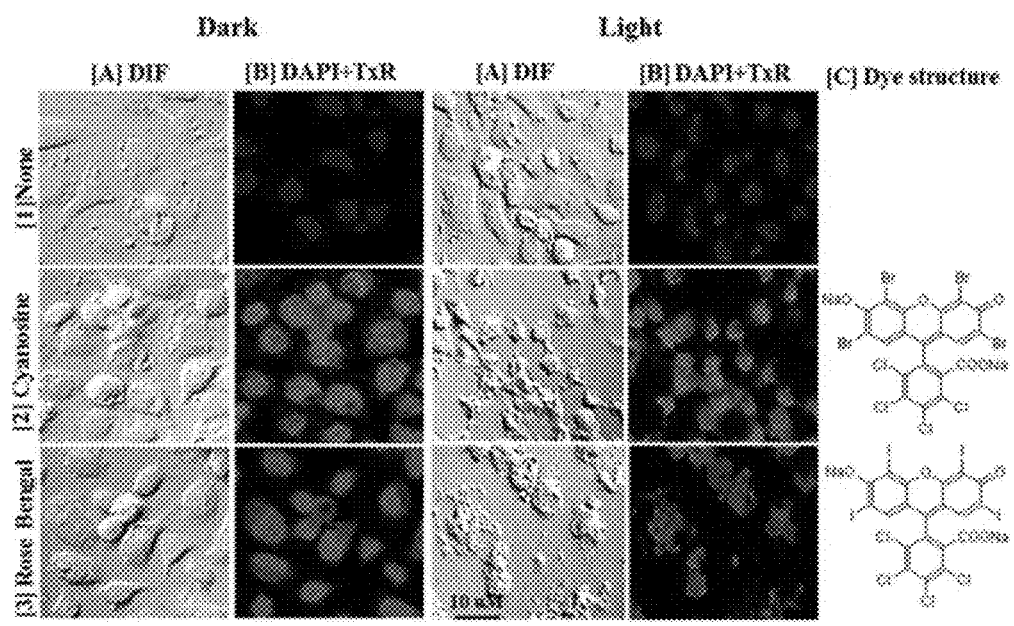
FIG. 2 shows uptake of cyanosine and rose bengal dyes by Aedes mosquito cells of the C6/36 line and their photosensitivity in vitro. The insect cells were exposed to both dyes overnight and illuminated with white light under conditions similar to those described for mammalian and *Leishmania* cells [19-21, 23]. Images were captured first under differential interference (DIF) [A] and then under the filter sets for DAPI and Texas red [B]. [C] Chemical structure of cyanosione and rose Bengal. Uptake of both dyes by the cells after incubation in the dark overnight (Dark, A2-3, B2-3) and cellular disintegration after light exposure for 4 hrs (Light, A2-3, B2-3) in contrast to the untreated controls (Dark and Light, A1, B1).

Methods and compositions disclosed herein comprising PSs may be used to combat, control, and/or reduce populations of insects. The insect populations which may be combated, controlled, and/or reduced by the methods and compositions of the disclosure include insects associated with the transmission of diseases of man and animals, as well as, for example, those associated with agriculture (which term includes the growing of crops for food and fiber products, horticulture and animal husbandry), forestry, and the storage of products of vegetable origin, such as fruit, grain and timber.

Where application of PS to the locus of the insects is desired, compositions which include PS and one or more suitable inert diluent, carrier materials, and/or surface active agents are formulated and applied. The compounds of the invention may be the sole active ingredient of the composition or they may be admixed with one or more additional active ingredients such as attractants (pheromones), insecticides, insecticide synergists, herbicides, fungicides or plant growth regulators where appropriate. Suitable additional active ingredients for inclusion in admixture with the compounds of the invention may be compounds which will broaden the spectrum of activity of the compounds of the invention or increase their persistence in the location of the insect. They may synergise the activity of the compounds of the invention or complement the activity for example by increasing the speed of effect, improving knockdown or overcoming repellency.

Examples of suitable insecticide synergists for use in the compositions include piperonyl butoxide, sesamex, and dodecyl imidazole. Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insects to be controlled, and the effects required from the mixture. However in general, the additional active ingredient of the composition will be applied at about the rate it would usually be employed if used on its own, or at a lower rate if synergism occurs.

Alternatively the compositions may be in the form of liquid preparations to be used as aerosols, dips, or sprays. Dips and sprays are generally aqueous dispersions or emulsions of the active ingredient in the presence of one or more known wetting agents, dispersing agents or emulsifying agents (surface active agents). Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may alternatively be prepared by dissolving the active ingredient in a suitable solvent, for example, water, dimethyl sulfoxide (DMSO), alcohol solutions, such as solutions comprising methanol, ethanol, isopropanol, etc., and other aqueous solutions.

EXAMPLES

The Examples that follow are illustrative of specific embodiments of the invention, and various uses thereof. They are set forth for explanatory purposes only, and are not to be taken as limiting the invention.

Example 1

Delivery of Representative PSs for PDI Against Selected Insects

*Culex pipiens quinquefasciatus* 4th instar larvae were exposed to rose Bengal or cyanosine (10 μg/mL) (~20 larvae/5 mL water/well in 6-well plate) in the dark for ~24 hours followed by exposure to white light for ~6 hrs at ~2500 lux; *Phlebotomus duboscqi* female (FIG. 1, panel B) and male (FIG. 1, panel C) adult flies (~20 flies/screened paper cup) fed with 5% sucrose solution and 500 μL of 5 mg/ml rose bengal in a cotton ball for ~20 hrs in the dark followed by exposure to ~2500 lux of white light for 3 hrs. Duplicate samples were prepared and kept in the dark as controls.

Results are shown in FIG. 1. Rose bengal was taken up by the flies of both sexes. Phototoxicity was especially evident for the mosquito larvae. The dyes were concentrated in the gut of the larvae kept in dye-containing water (FIG. 1, panel A). Both dyes were clearly visible in the abdomen of both female and male sand flies (FIG. 1, panels B and C, respectively) after feeding on dye+sucrose solutions soaked in cotton balls. These PSs are thus not repulsive to the feeding and taste of the flies.

The susceptibility of PS-sensitized insects to white light illumination varied with the species and the PSs used. The motility of mosquito larvae provides a robust assay to assess their viability after PS-sensitization followed by light illumination. Comparison of PS-sensitized mosquito larvae kept in the dark and those exposed to light provided evidence of photo-inactivation to various extents as a function of exposure time in all cases (FIGS. 3-4).

Differences were significant for the RB- and CY-sensitized larvae between dark and light conditions.

These data demonstrate uptake and toxicity of PS in sand flies and mosquitos.

Example 2

Uptake of PS by Mosquito Cells In Vitro

Uptake of PS was assessed in insect cells, specifically Aedes albopictus clone C6/36 (ATCC CRL-1660). The insect cells were exposed to both dyes overnight and illuminated with white light under conditions similar to those described for mammalian and Leishmania cells. FIG. 2 shows the uptake of RB and CY dyes by these mosquito cells, rendering them sensitive to photo-inactivation. Images were captured first under differential interference (DIF) [A] and then under the filter sets for DAPI and Texas red [B]. [C] Chemical structure of cyanosione and rose Bengal.

Untreated cells ([1]-None) were adherent (1A-DIF) and non-fluorescent (1B DAPI+TxR), irrespective of illumination (1 Dark and Light). Cells exposed to CY [2] and RB [3] showed cytoplasmic fluorescence (2B, 3B DAPI-txR), indicative of dye uptake. Sensitized cells remained adherent and intact (Dark, 2A, 3A-DIF), but became disintegrated after light exposure (Light, 2A, 3A-DIF). These results are consistent with the larvicidal activities of RB and CY, providing a cellular basis for their PDT activities.

Example 3

Mosquito Larvicidal Activities of Light-Activated Phthalocyanines and Porphyrin Derivatives The mosquito larvicidal activities were tested for the phthalocyanine and porphryin derivative PSs shown in Table 1, which shows the full chemical name, structure, and PS abbreviation for each compound.

$2^{nd}$ to $4^{th}$ instar larvae of A. aegypti and A. albopictus (or Aedes mosquitoes in brief) were used in the experiments, as they are known vectors of Zika fever and other viral diseases. Colonies of both species were reared to provide the larvae of all instars under the approved conditions of a humidified "warm room" (~28 C, ~80% relative humidity).

The PDI assay to determine the larvicidal activities of the PS in Table 1 was based on procedures developed for mammalian and protozoa cells with modifications for mosquito larvae. Briefly, each PS was tested in 3-4 concentrations in 10-fold serial dilutions, starting with a 1/100 dilution of the stock solution (see Table 1 for the PS stock concentrations) as the highest. The solvent (DMSO) at these PS concentrations was ≤1%, which was pre-tested alone and shown to have no larvicidal activity. Larvae were PS-exposed (and not exposed as a control) in groups of 20 per 5 mL of water per well of a 6-well plate, in duplicate. All plates were foil-wrapped for overnight incubation under dark conditions in the "warm room." After 16 hours of PS exposure, one of the duplicate 6-well plates was un-wrapped and the lid removed for exposure from the top with white light from a fluorescent tube-containing box (1-2 $J/cm^2$). The remaining 6-well plate of the duplicate was exposed under exactly the same conditions, but remained foil-wrapped as the dark control. Larvae were checked for mobility and readings recorded hourly for up to 7 hours. This is a reliable parameter to assess larvicidal activities, since immobilized larvae invariably failed to regain their motility and perished upon further incubation. All larvae were found to remain viable under the dark conditions based on this criterion. Each condition was repeated 4-5 times in independent experiments.

Figure 3A:
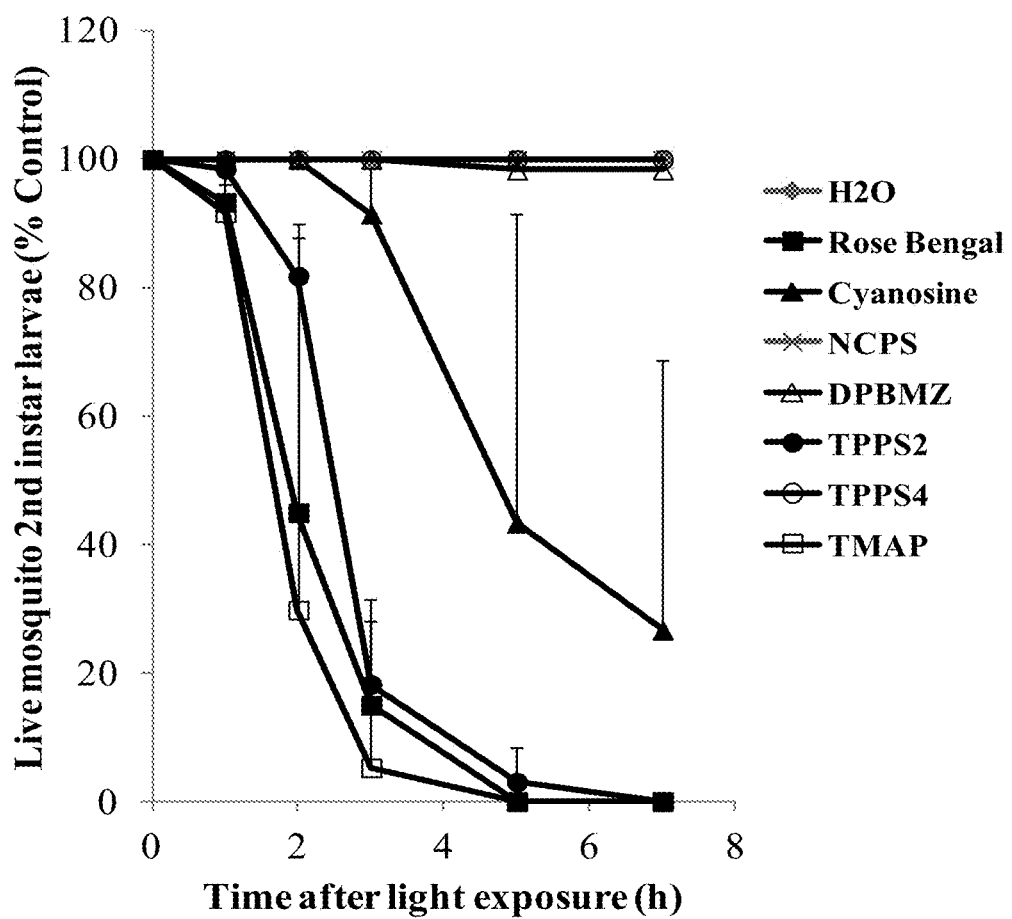
FIG. 3A shows sensitivity of $2^{nd}$ instar *Aedes* mosquito larvae to light-activated porphyrins.
Figure 3B:
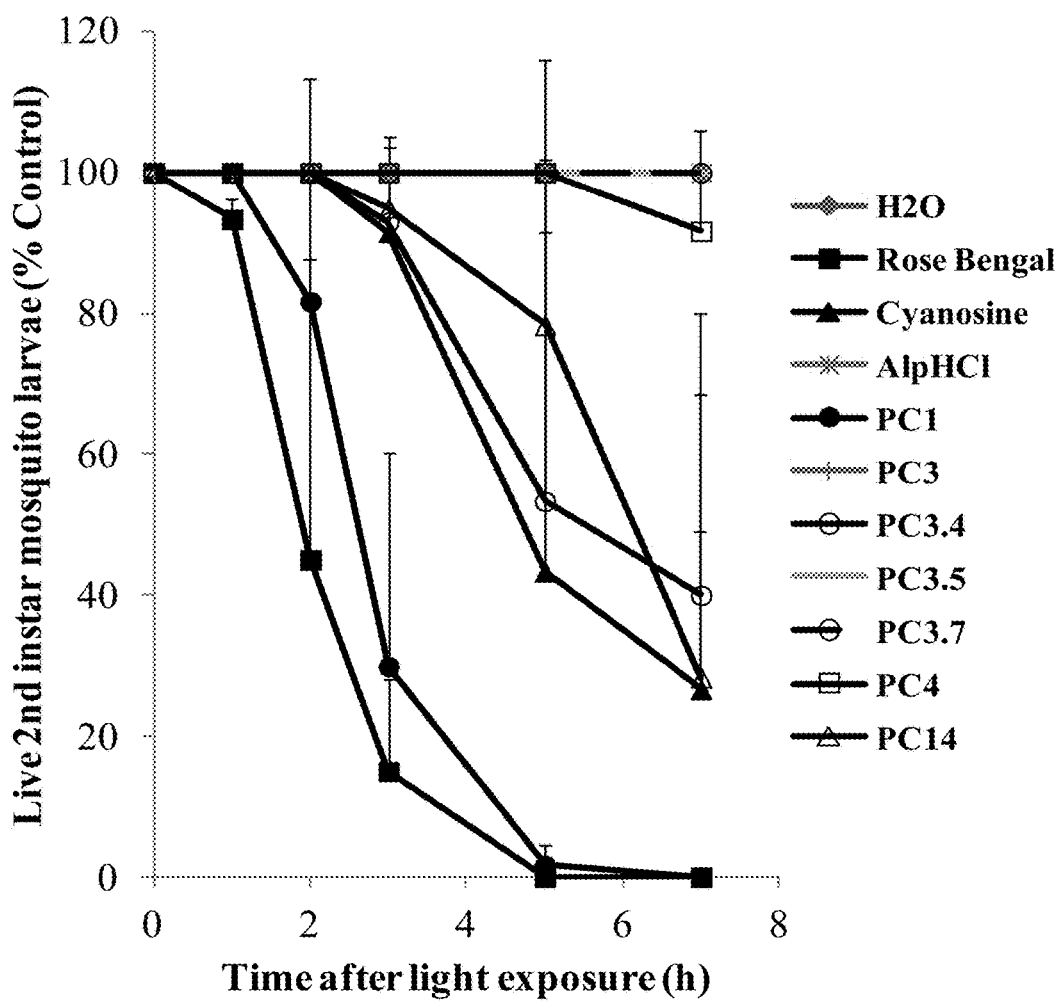
FIG. 3B shows sensitivity of $2^{nd}$ Instar *Aedes* mosquito larvae to light-activated phthalocyanines. RB and CY are included for comparison.

FIG. 3 shows the results for PS type-mediated and time-dependent $2^{nd}$ instar larvicidal activities for five porphyrin derivatives (FIG. 3A) and eight phthalocyanines (PC) (FIG. 3B), all using 1/1000 dilution for each of the stock solutions (Table 1). Included for comparison were negative controls without PS ($H_2O$) and positive controls with RB and CY (cf. FIG. 1). Of the five porphyrins examined, TMAP (open squares) and TPPS2 (solid circles) produced results most similar to RB (solid squares), and results demonstrating more larvicidal activity than CY (solid triangles), as measured by % of dark control in larva immobilization, starting and reaching completion during the period of illumination from 2 to 7 hours (FIG. 3A). Of the eight PCs examined under the similar conditions, PC1 (solid circle) and PC2 (not shown) were similar to RB (solid squares) in larvicidal activity, while PC14 (open triangles) and PC3.4 (open circles) produced results akin to CY (closed triangle), in the kinetics of their larvicidal activities (FIG. 3B). All of the effective porphyrins and PCs were more potent than the positive controls, especially CY, as indicated by the disparity of their stock concentrations (Table 1).

TABLE 1

Dyes tested for light-activable Aedes mosquito larvicidal activities

| Dye | Excit. wavelength (nm) | Molecular Weight | Solvent | Stock Conc. (mM) | Structure |
|---|---|---|---|---|---|
| RB Rose Bengal | 550 | 1017.85 | Water | 49.1 | 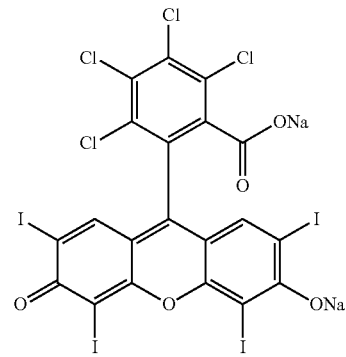 |

TABLE 1-continued

Dyes tested for light-activable Aedes mosquito larvicidal activities

| Dye | Excit. wavelength (nm) | Molecular Weight | Stock Solvent | Stock Conc. (mM) | Structure |
|---|---|---|---|---|---|
| CY Cyanosine | 550 | 829.66 | Water | 60.3 | 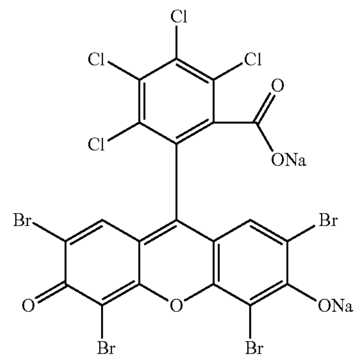 |
| AlPHCl | ~600 | 574.96 | DMSO | 1.7 | 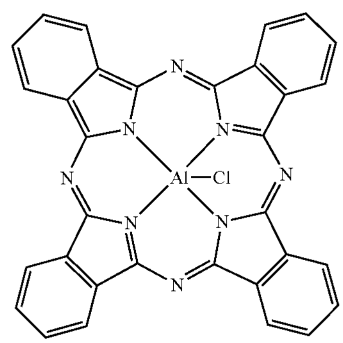 |
| PC1 $C_{40}H_{36}N_{10}O_2Si$ | ~600 | 716.87 | DMSO | 1.0 | 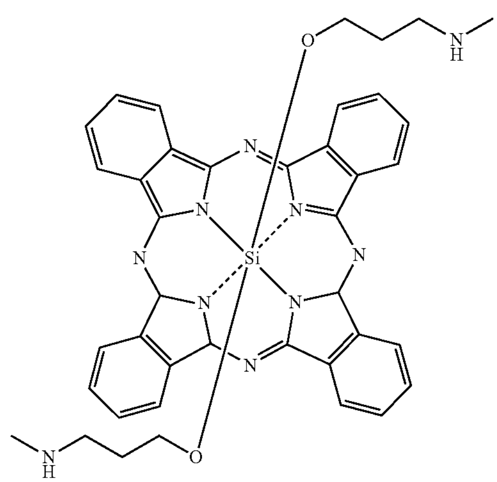 |

TABLE 1-continued

Dyes tested for light-activable Aedes mosquito larvicidal activities

| Dye | Excit. wavelength (nm) | Molecular Weight | Solvent | Stock Conc. (mM) | Structure |
|---|---|---|---|---|---|
| PC2 $C_{46}H_{50}N_{12}O_2Si$ | ~600 | 831.05 | DMSO | 1.0 | |
| PC3 $C_{44}H_{42}N_8O_8Si$ | ~600 | 838.94 | DMSO | 1.0 | |
| PC4 $C_{46}H_{44}N_8O_8Zn$ | ~600 | 902.28 | DMSO | 1.0 | |

TABLE 1-continued

Dyes tested for light-activable Aedes mosquito larvicidal activities

| Dye | Excit. wavelength (nm) | Molecular Weight | Stock Solvent | Stock Conc. (mM) | Structure |
|---|---|---|---|---|---|
| PC3.4 R = N(CH$_3$)$_3$I | ~600 | 1242.19 | DMSO | 1.0 | 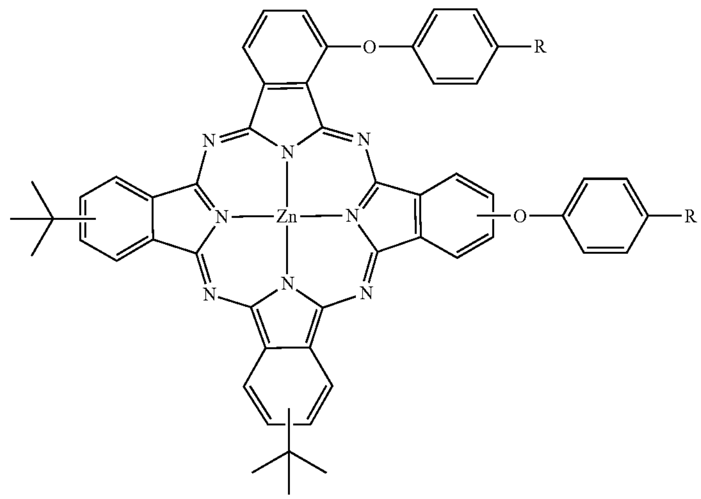 |
| PC3.5 R = N(CH$_3$)$_3$I | ~600 | 1242.19 | DMSO | 1.0 | 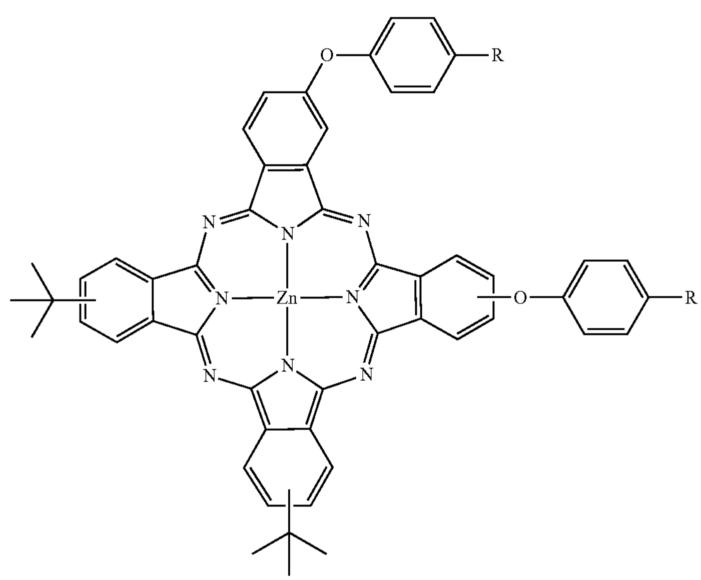 |

TABLE 1-continued

Dyes tested for light-activable Aedes mosquito larvicidal activities

| Dye | Excit. wavelength (nm) | Molecular Weight | Stock Solvent | Stock Conc. (mM) | Structure |
|---|---|---|---|---|---|
| PC3.7 R = N(CH$_3$)$_3$I | ~600 | 1684.06 | DMSO | 1.0 | 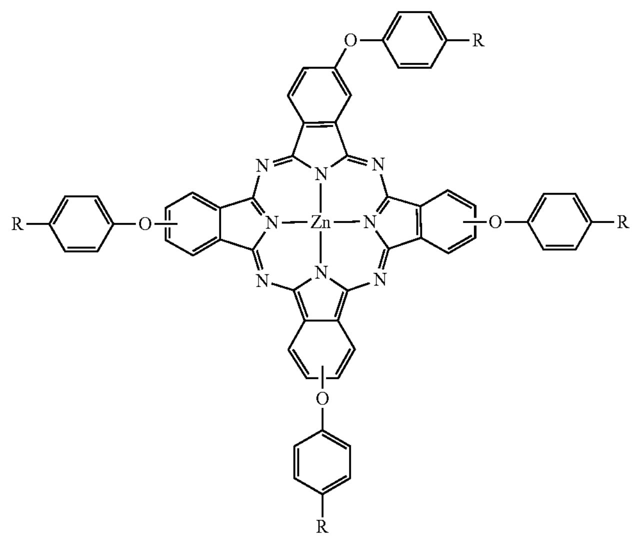 |
| PC14 M = Si L = OSi(C$_6$H$_5$)$_2$C(CH$_3$)$_3$ R = CH$_3$ | ~600 | | DMSO | 1.0 | 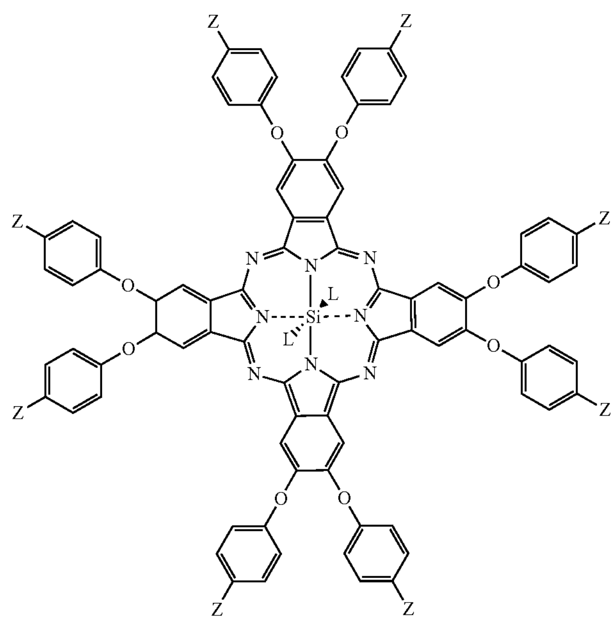 |
| BPDZM M-Benziporphodimethene | ~400 | 594.188 | Water/DMSO | 1.0 | |

TABLE 1-continued

Dyes tested for light-activable Aedes mosquito larvicidal activities

| Dye | Excit. wave-length (nm) | Molecular Weight | Stock Solvent | Stock Conc. (mM) | Structure |
|---|---|---|---|---|---|
| NCPS Meso-tetrakis(p-sulfonato-phenyl) N-confused porphyrin tetrasodium | ~400 | 1022.9 | Water/ DMSO | 1.0 | NCPS |
| TPPS4 Meso-tetra(4-sulfonato-phenyl) porphine Tetrasodium | ~400 | 1239.1 | Water/ DMSO | 1.0 | 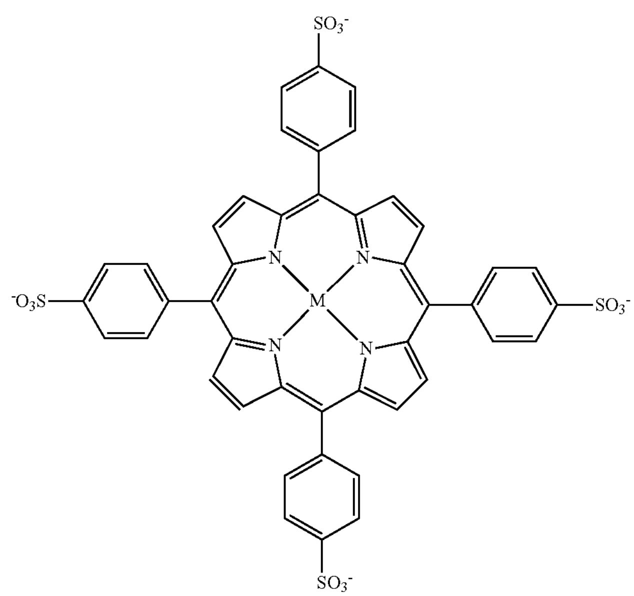 |
| TMAP Meso-tetra(4-n,n,n-trimethylanili-nium) porphine tetrachloride | ~400 | 988.96 | Water/ DMSO | 10.0 | 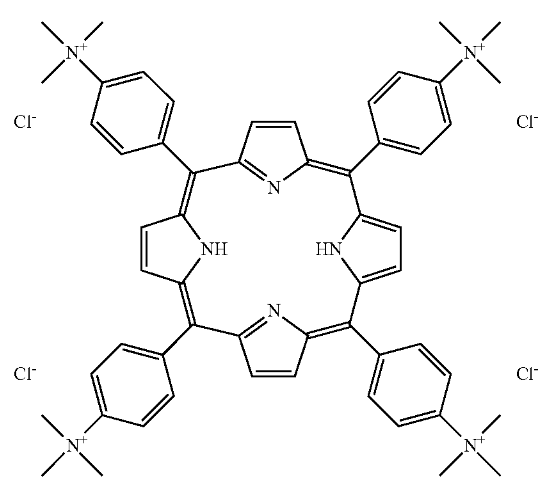 |

TABLE 1-continued

Dyes tested for light-activable Aedes mosquito larvicidal activities

| Dye | Excit. wavelength (nm) | Molecular Weight | Solvent | Stock Conc. (mM) | Structure |
|---|---|---|---|---|---|
| TPPS2 Meso-Tetraphenylporphine disulphonic acid dihydrochoride | ~400 | 847.78 | Methanol | 2.0 | |

Figure 4A:
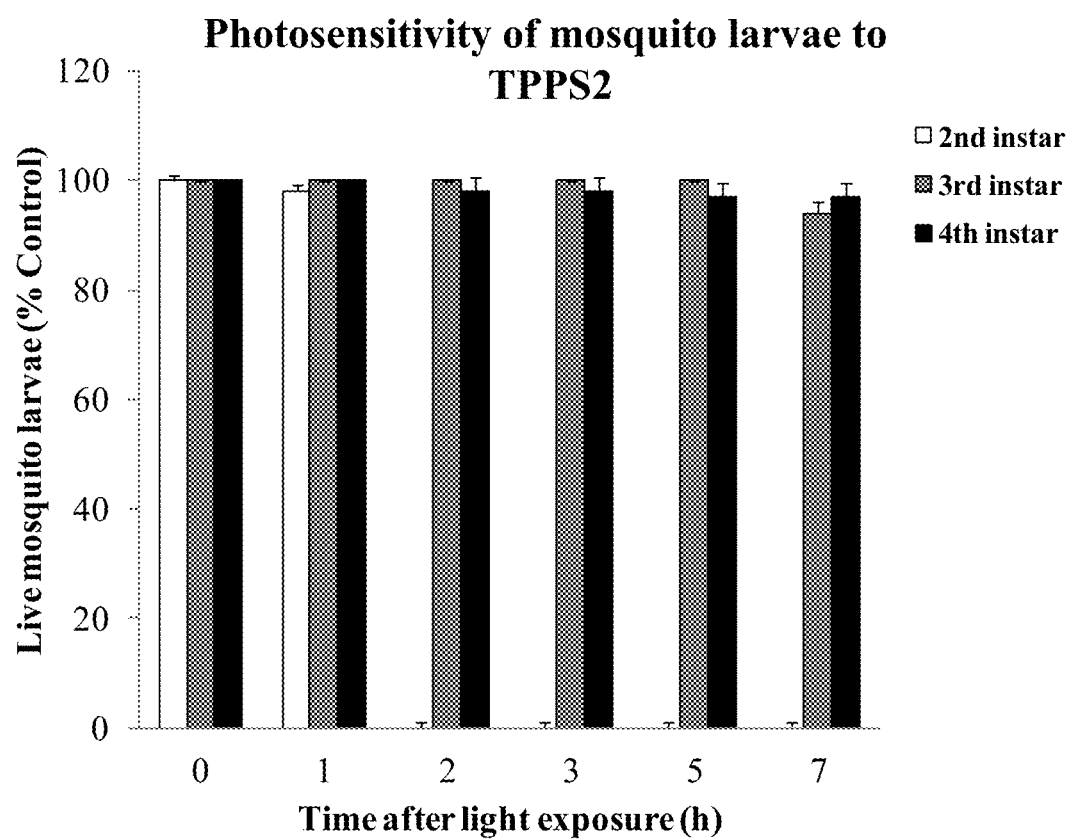
FIGS. 4A-4E show instar-specific sensitivity of Aedes mosquito larvae to light-activated photosensitizers. Specifically.
Figure 4B:
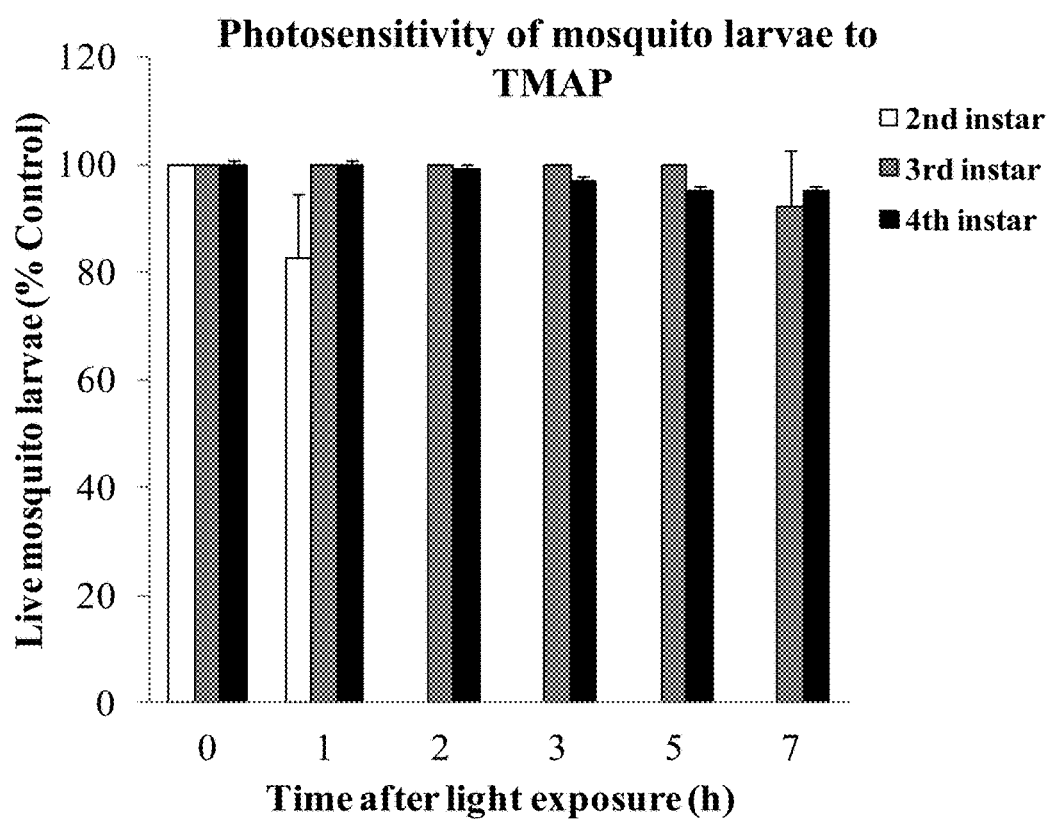
Figure 4C:
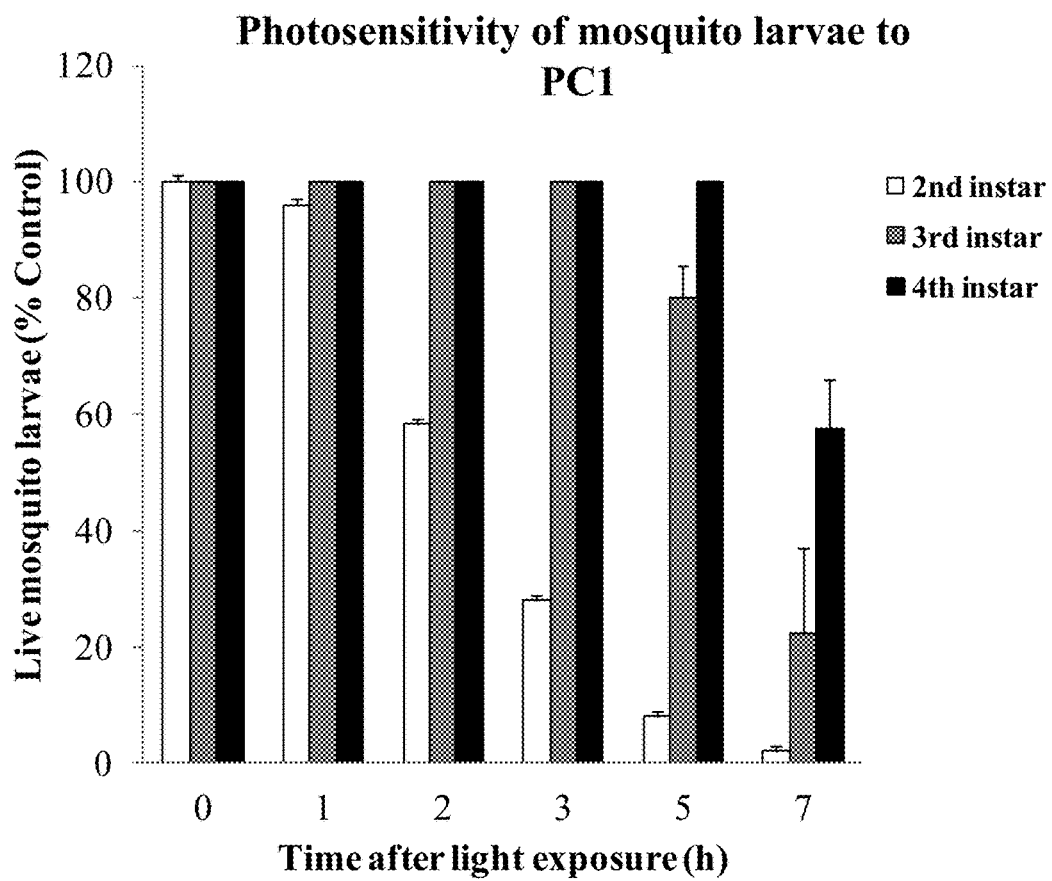
Figure 4D:
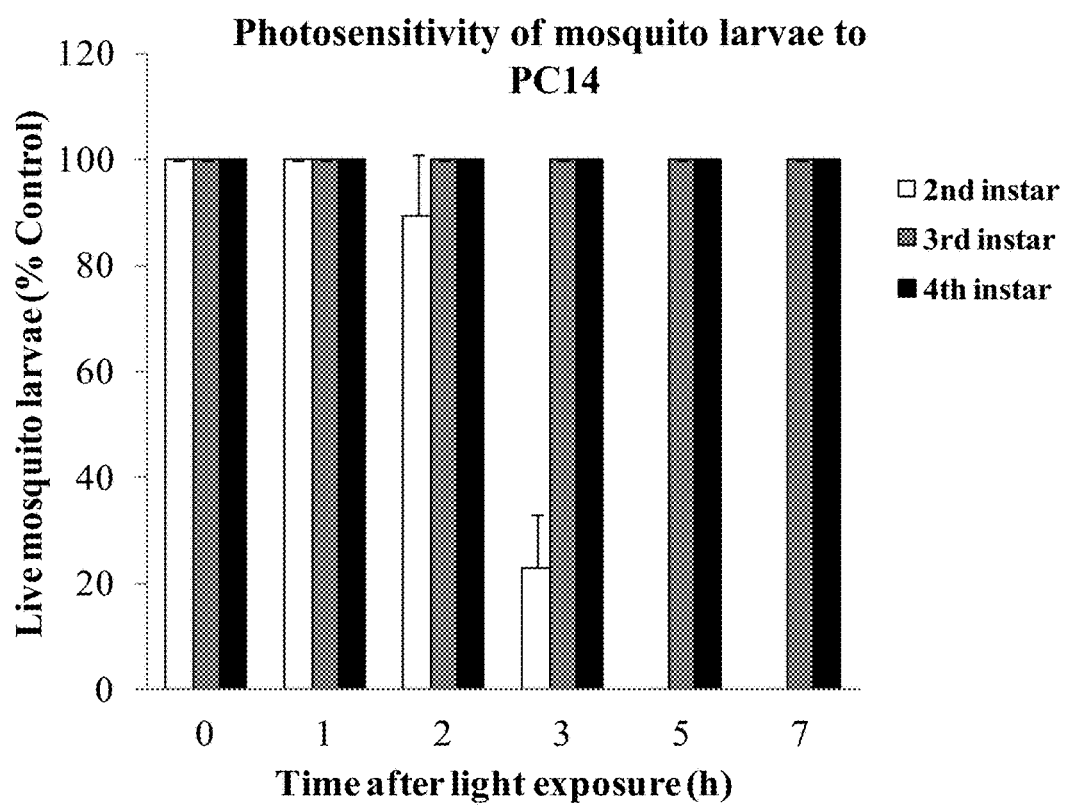
Figure 4E:
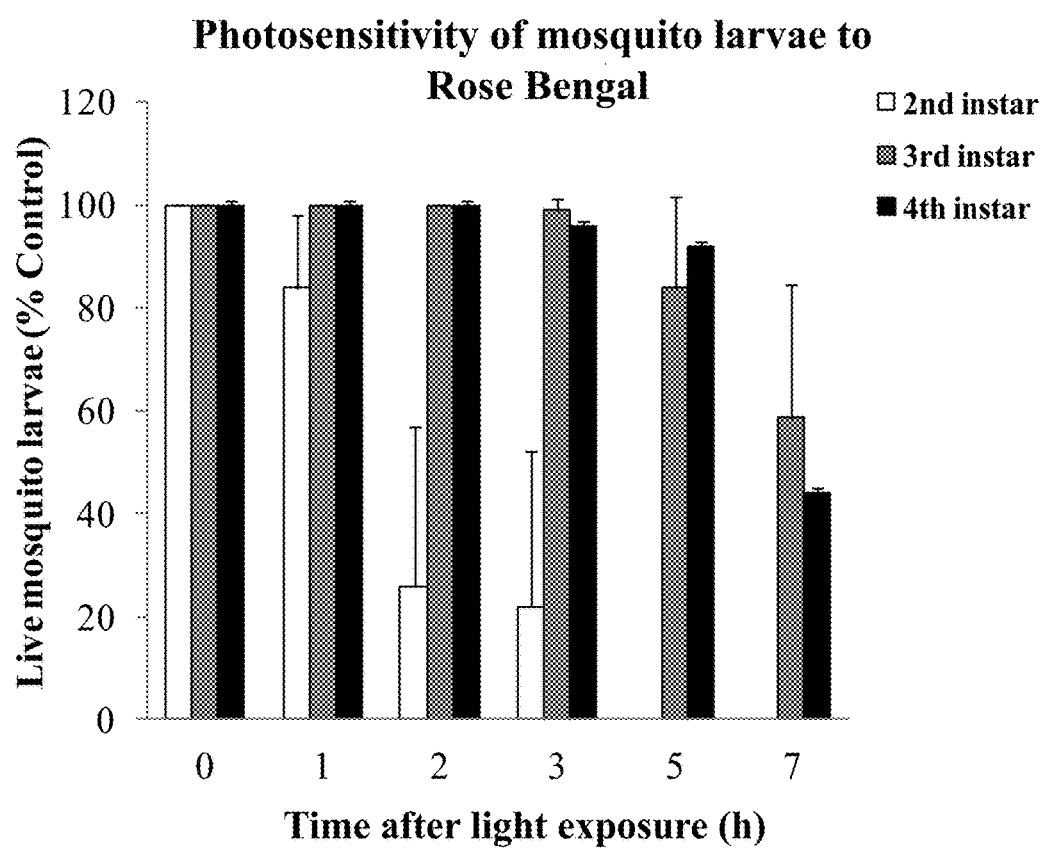

Instar-dependent sensitivity of *Aedes* mosquito larva to effective PDI: Representative porphyrins and PCs found effective (FIG. 3) were each further assessed for PDI activities against $2^{nd}$ to $4^{th}$ instar larvae at 1/10000 dilution of the stocks (FIG. 4). Under these conditions, TPPS2, TMAP and PC14 were found to kill only $2^{nd}$ instar larvae completely in 2-5 hours, leaving the other instars unscathed (FIGS. 4A, 4B, and 4D); PC1 and RB reduced the viability of all instars to a variable extent with decreasing effectiveness against older larvae (FIGS. 4C, 4E).

$EC_{50}$ of the effective dyes for PDT-mediated larvicidal activities: The EC50 value for each effective PS was estimated from its concentration vs. larvicidal activity curve for the $2^{nd}$ instar larvae (Table 2). The most effective were PC1 and TPPS2 with $EC_{50}$ in the range of 35-80 nM. The remainder of the compounds were in the range of 100-400 nM, except for cyanosine, which was the least effective with an $EC_{50}$ of 30 µM.

TABLE 2

EC50s of effective dyes for PDT-mediated Ades $2^{nd}$-instar larvicidal activities.

| Photosensitizer | $EC_{50}$ (nM) |
|---|---|
| Rose Bengal | 250 |
| Cyanosine | 30,000 |
| TPPS2 | 80 |
| TMAP | 100 |
| PC1 | 35 |
| PC 3.4 | 400 |
| PC14 | 100 |

Based on these results, photodynamic insecticides (PDI) represent a safe and effective approach for pest control, which in some embodiments may be used complementary to chemical insecticides and GMO release technology. Many PS for PDI are non-toxic compounds, and yet their application for PDI is not expected to select for resistance in contrast to the chemical pesticides in current use. In some embodiments, PDI can be used to complement the GM approaches in the field of agriculture and medicine.

These data demonstrate the identification of five new PS with *Aedes* larvicidal activities in nanomolar concentrations in combination with dim light.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method for reducing an insect population, the method comprising:
   (a) contacting the insect population with a photosensitizer, wherein the photosensitizer is a compound of formula (I):

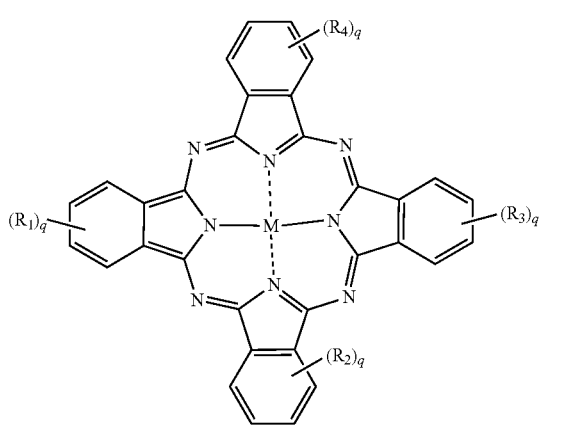

or an acceptable salt thereof, wherein

M is Zn or $Si(L_1)(L_2)$;

$L_1$ and $L_2$ are independently selected from —O($C_1$-$C_6$alkyl), —O($C_1$-$C_6$alkenyl), —O($C_1$-$C_6$alkynyl), —NH($C_1$-$C_6$alkyl), —N($C_1$-$C_6$alkyl)$_2$, and —OR, wherein each R is independently —[$C_1$-$C_6$alkylene-O]$_m$-R', —[$C_1$-$C_6$alkylene-NR"]$_n$—R', or —Si(R''')$_3$, each m and n are independently an integer selected from 1 to 20, each R' is independently selected from H and $C_1$-$C_6$alkyl, each R" is independently selected from H and $C_1$-$C_6$alkyl, each R''' is independently selected from H, $C_1$-$C_6$alkyl, and aryl;

each q is independently an integer selected from 0, 1, and 2; and $R_1$, $R_2$, $R_3$, and $R_4$ are independently selected from halogen, $C_1$-$C_6$ alkyl, $C_1$-$C_6$alkenyl, $C_1$-$C_6$alkynyl, —NH($C_1$-$C_6$alkyl), —N($C_1$-$C_6$alkyl)$_2$, $C_1$-$C_6$alkoxy, $C_1$-$C_6$aryloxy, $C_1$-$C_6$heteroaryloxy, and polyalkylene oxide, each optionally substituted with one or more of halogen, $C_1$-$C_6$alkyl, —OH, $C_1$-$C_6$alkoxy, —NH$_2$, —NH($C_1$-$C_6$alkyl), —N($C_1$-$C_6$alkyl)$_2$, —N($C_1$-$C_6$alkyl)$_3$(I), —N($C_1$-$C_6$alkyl)$_3$(Cl), or —N($C_1$-$C_6$alkyl)$_3$(F);

or the photosensitizer is a compound of formula (II):

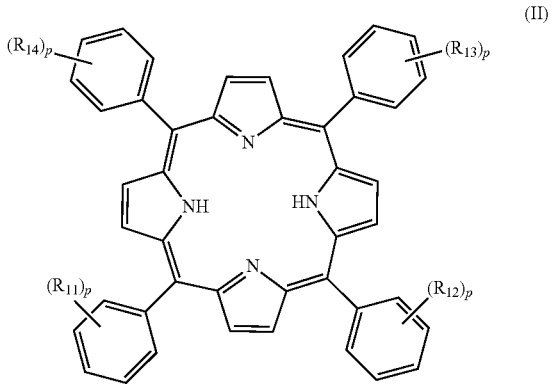

(II)

or an acceptable salt thereof, wherein each p is independently an integer selected from 0, 1, and 2; and $R_{11}$, $R_{12}$, $R_{13}$, and $R_{14}$ are independently selected from the group consisiting of: halogen, $C_1$-$C_6$alkyl, $C_1$-$C_6$alkenyl, $C_1$-$C_6$alkynyl, $C_1$-$C_6$alkoxy, —NH($C_1$-$C_6$alkyl), —N($C_1$-$C_6$alkyl)$_2$, —N($C_1$-$C_6$alkyl)$_3$ (I), —N($C_1$-$C_6$alkyl)$_3$(Cl), —N($C_1$-$C_6$ alkyl)$_3$(F), —S(O)$_2$(OH), and —S(O)$_2$($C_1$-$C_6$alkoxy), wherein the photosensitizer is internalized by larval and/or adult insects within the insect population, and wherein the photosensitizer produces reactive oxygen species upon excitation by light; and (b) exposing the photosensitized insect population to light in the presence of oxygen to reduce the insect population.

2. The method of claim 1, wherein the photosensitizer is selected from the group consisting of: PC1, PC2, PC3.4, PC14, TMAP, and TPPS2.

3. The method of claim 2, wherein the photosensitizer is selected from the group consisting of PC1, PC2, PC3.4, and PC14.

4. The method of claim 1, wherein the light is white light or red light.

5. The method of claim 1, wherein the insect population comprises *Anopheles* spp., *Aedes* spp., *Culex* spp., *Coquilletidia* spp., *Phlebotomus* spp., *Simulium* spp., or *Culicoides* spp. insects.

6. The method of claim 1, wherein the insect population comprises hematophagus insects.

7. The method of claim 1, wherein the photosensitizer is internalized by $2^{nd}$, $3^{rd}$, and/or $4^{th}$ instar larval insects.

8. The method of claim 1, wherein the photosensitizer is the compound of formula (I), which is of formula:

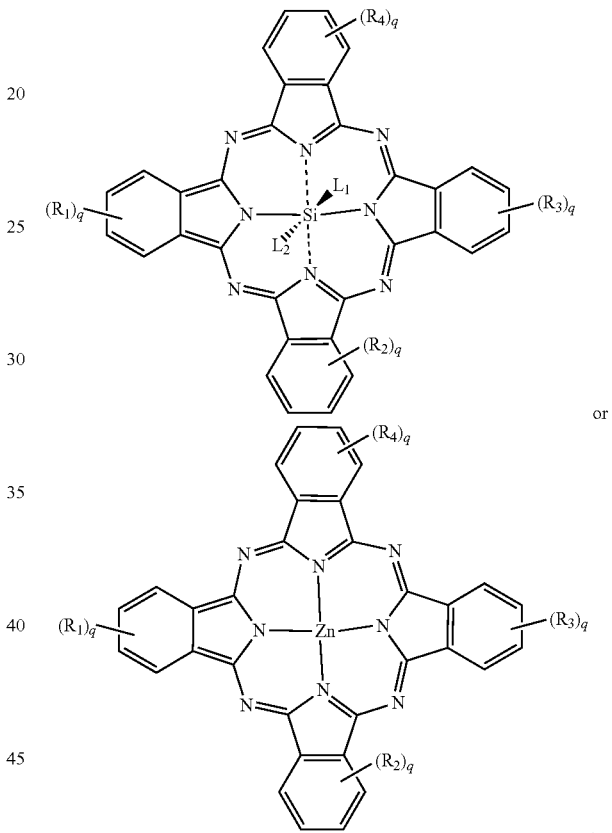

or

9. The method of claim 1, wherein each q in formula (I) is an integer selected from 0 and 1; and/or wherein $L_1$ and $L_2$ are independently selected from —O($C_1$-$C_6$ alkyl), —O($C_1$-$C_6$ alkenyl), —O($C_1$-$C_6$ alkynyl), and —OR; and/or wherein each R is independently —[$C_1$-$C_6$ alkylene-NR"]$_n$-R', or —[ethylene-NR"]$_n$-R'or —[propylene-NR"]$_n$-R'; wherein R" is hydrogen or methyl, or R" is hydrogen; and wherein R' is hydrogen or methyl, or R' is hydrogen, or R' is methyl; and/or wherein n is an integer selected from 1 to 6, or from 1 to 5, or from 1 to 4, or from 1 to 3, or n is 1, 2, or 3, or n is 1, or n is 2, or n is 3; and/or wherein each R is independently —Si(R''')$_3$, wherein R''' is independently selected from H, $C_1$-$C_6$ alkyl, and aryl; or wherein R''' is independently selected from $C_1$-$C_6$ alkyl and aryl.

10. The method claim 1, wherein $L_1$ and $L_2$ are independently selected from:
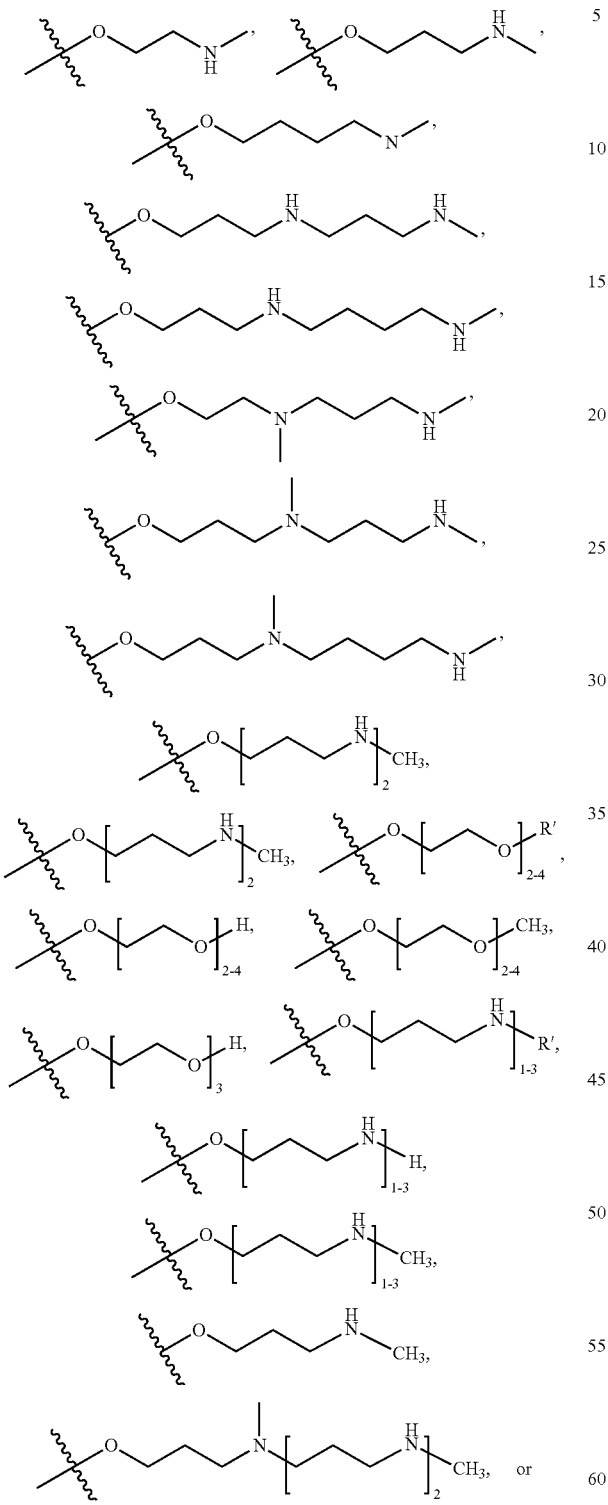
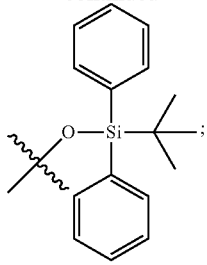
and/or wherein $L_1$ and $L_2$ are the same.
11. The method of claim 1, wherein the photosensitizer is the compound of formula (II), which is of formula:
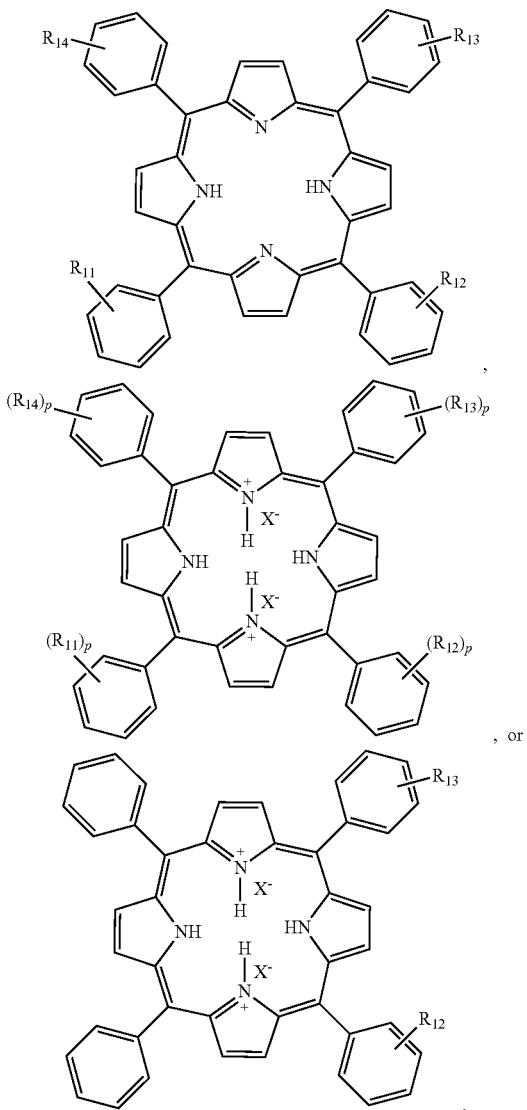
* * * * *